US010212798B2

(12) United States Patent
Alavi et al.

(10) Patent No.: US 10,212,798 B2
(45) Date of Patent: Feb. 19, 2019

(54) TORCH FOR INDUCTIVELY COUPLED PLASMA

(71) Applicants: Sina Alavi, North York (CA); Javad Mostaghimi, Mississauga (CA)

(72) Inventors: Sina Alavi, North York (CA); Javad Mostaghimi, Mississauga (CA)

( * ) Notice: Subject to any disclaimer, the term of this patent is extended or adjusted under 35 U.S.C. 154(b) by 0 days.

(21) Appl. No.: 15/882,415

(22) Filed: Jan. 29, 2018

(65) Prior Publication Data
US 2018/0220520 A1 Aug. 2, 2018

Related U.S. Application Data

(60) Provisional application No. 62/452,083, filed on Jan. 30, 2017, provisional application No. 62/614,892, filed on Jan. 8, 2018.

(51) Int. Cl.
*H01J 7/24* (2006.01)
*H05B 31/26* (2006.01)
*H05H 1/30* (2006.01)
*G01J 3/443* (2006.01)
*G01N 21/73* (2006.01)
*H01J 49/10* (2006.01)
*H05H 1/46* (2006.01)

(52) U.S. Cl.
CPC ............ *H05H 1/30* (2013.01); *G01J 3/443* (2013.01); *G01N 21/73* (2013.01); *H01J 49/105* (2013.01); *H05H 1/46* (2013.01)

(58) Field of Classification Search
CPC .. H05H 1/46; H05H 1/24; H05H 1/54; H05H 1/52; H05H 15/00; H01J 37/32082; H01J 37/32192; H01J 37/32174; H01J 37/321; H01J 37/3211; H01J 37/32623; H01J 41/04; H01J 41/14; H01J 41/06; F03H 1/00; F03H 1/0062; B82Y 10/00; H01T 23/00; H01T 19/00
See application file for complete search history.

(56) References Cited

U.S. PATENT DOCUMENTS

2005/0242070 A1* 11/2005 Hammer ................. G01N 21/73
219/121.48
2012/0261390 A1* 10/2012 Boulos ..................... H05H 1/28
219/121.49

* cited by examiner

*Primary Examiner* — Minh D A
(74) *Attorney, Agent, or Firm* — Nasser Ashgriz; UIPatent Inc.

(57) ABSTRACT

A torch for use in inductively coupled plasma is described. In the torch, a torch tube has an angular accelerator where a flow of gas experiences an increase in angular velocity. The torch tube also has a conical end where the increased angular velocity of the gas is encouraged to accelerate into a cavity that can support the plasma. In various examples, the conical end of the torch tube comprising a conical gap that accelerates the axial velocity component of the gas flow.

22 Claims, 31 Drawing Sheets

3-Tube design: outer, intermediate, and injector
Gas consumption: ~14 – 17 L/min (12 – 15, 1, 1 L/min)
RF Power: ~ 1100 – 1600 W
Outer tube I.D.: 18 mm
Cylindrical geometry

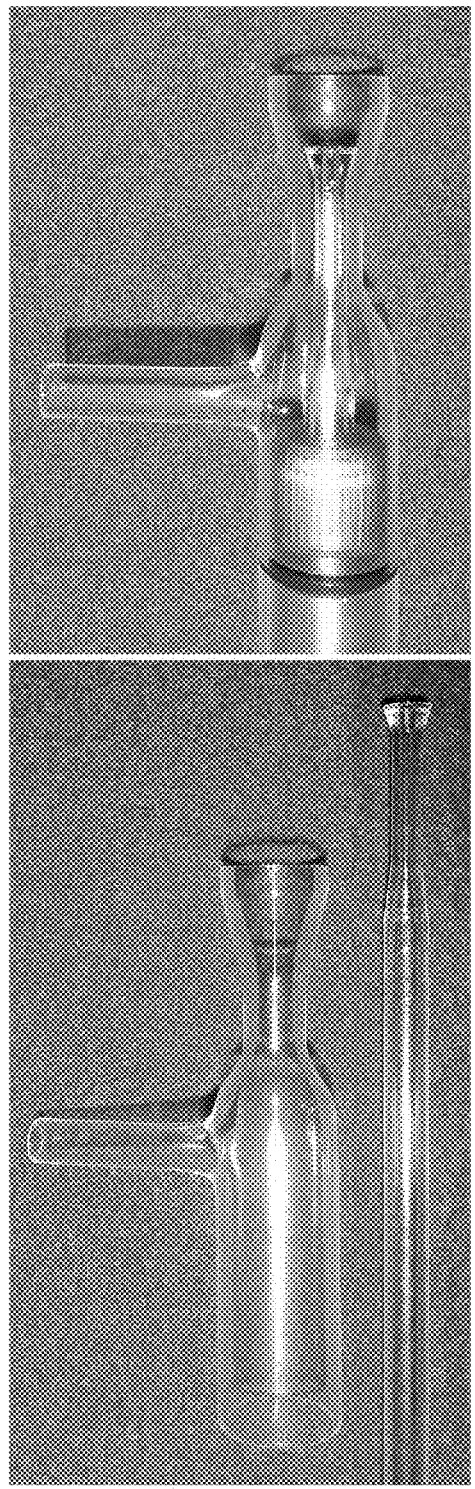

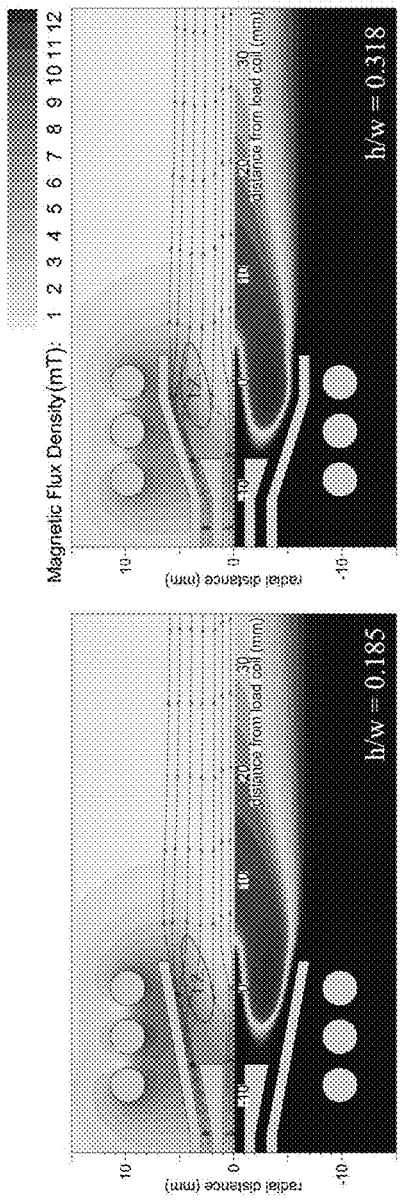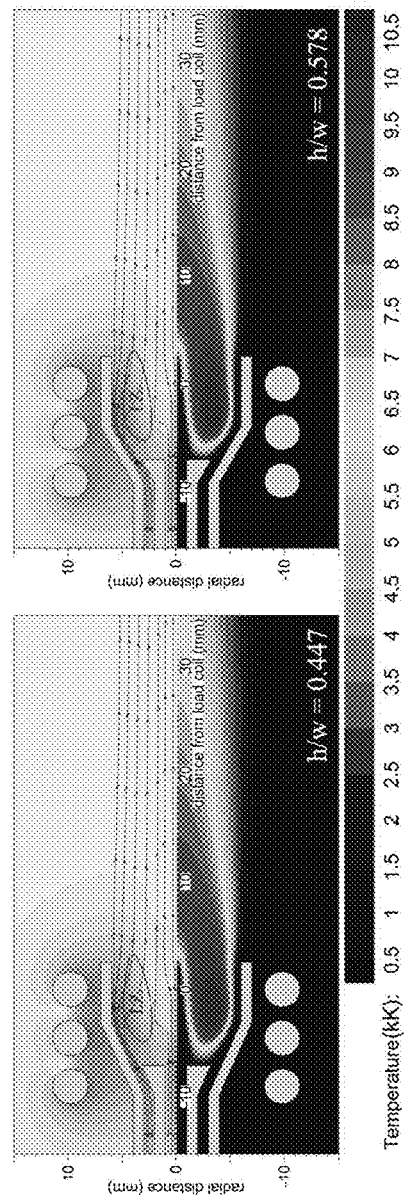
FIG. 26A  FIG. 26B
FIG. 26C  FIG. 26D

TORCH FOR INDUCTIVELY COUPLED PLASMA

CROSS REFERENCE TO RELATED APPLICATIONS

The present application claims the benefit of U.S. Provisional Patent Application No. 62/452,083 filed Jan. 30, 2017 and entitled "TORCH FOR INDUCTIVELY COUPLED PLASMA;" and U.S. Provisional Patent Application No. 62/614,892 filed Jan. 8, 2018 and entitled "TORCH FOR INDUCTIVELY COUPLED PLASMA," the disclosures of which are hereby incorporated by reference in their entirety.

FIELD OF THE INVENTION

This disclosure relates to a plasma torch device. In particular various embodiments describe are directed to a torch for Inductively Coupled Plasma Spectroscopy and Spectrometry.

BACKGROUND OF THE INVENTION

Inductively coupled plasma (ICP) is a high temperature source that is used for converting samples of substances in to a form that can be analyzed by various types of spectrometers. These spectrometers include mass spectrometers, atomic and optical emission spectrometers and other instruments used for both qualitative and quantitative analysis. The samples are typically comprised of substances dissolved in solution; a suspension of substances in a liquid; or solid substances carried within a gas flow.

In an ICP torch, the plasma is generated when a flow of gas, such as argon, is ionized in an intense electromagnetic field. When an optimal plasma temperature and energy density is generated, a sample that is introduced through the torch into the plasma can be vaporized, atomized, ionized, and/or excited prior to elemental analysis.

Generally, the conditions to achieve an optimal plasma temperature and energy density are reflected by the argon gas flow rate and the power intensity of the electromagnetic field. In most conventional ICP systems, the operation of the plasma torches required a significantly high argon gas flow, in excess of 16 liters per minute (I/m), and a radio frequency (RF) power in excess of 1 kW, typically between 1400 W and 1600 W, in order to generate a suitable electromagnetic field. As a consequence, the regular use of these ICP systems under these conditions can result in a significant operating cost.

SUMMARY OF THE INVENTION

In view of the foregoing and in accordance with the present teachings, the applicant recognizes that the ICP torch can be designed to operate with a lower gas flow rate and with a lower RF power requirement.

Accordingly, a torch for inductively coupled plasma is provided, comprising a torch tube having a support end and a conical end with a cavity for confining the plasma. An injector tube is positioned concentric within the torch tube so that the space between the concentric tubes defines an annular channel. The injector tube has an injector inlet end that is configured for receiving a sample flow and an injector conical end that is configured for passing the sample flow into the cavity. The conical end of the torch tube is configured to correspond with the injector conical end so that a conical gap is formed there between and extends through at least a portion of the conical end. The torch tube also has a gas inlet for receiving a gas flow, the gas inlet being configured for passing the gas tangentially into the annular channel with an angular velocity. The torch tube further comprising an elongated neck formed between the support end and the conical end. A portion of the elongated neck defines an angular accelerator that is configured for increasing the angular velocity of the gas flowing from the gas inlet downstream to the conical end, and discharging parallel through the conical gap.

The term embodiment and like terms are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, not this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

Embodiments of the present disclosure include a torch for inductively coupled plasma, the torch comprising of a torch tube having a support end and a conical end, wherein a portion of the conical end defines a cavity for confining the inductively coupled plasma; an injector tube positioned within the torch tube, wherein the injector tube includes an injector inlet end for receiving a sample flow and an injector conical end; and an annular channel defined between an outer wall of the injector tube and an inner wall of the torch tube, wherein the torch tube further comprises a gas inlet for receiving a gas flow.

DRAWINGS

The skilled person in the art will understand that the drawings, described below, are for illustration purposes only. The drawings are not intended to limit the scope of the applicant's teachings in any way.

FIG. 14A shows injector and outer tubes for the new torch shown separately.

FIG. 14B shows injector and outer tubes as mounted on a polycarbonate torch holder.

Figures 15A, 15B:
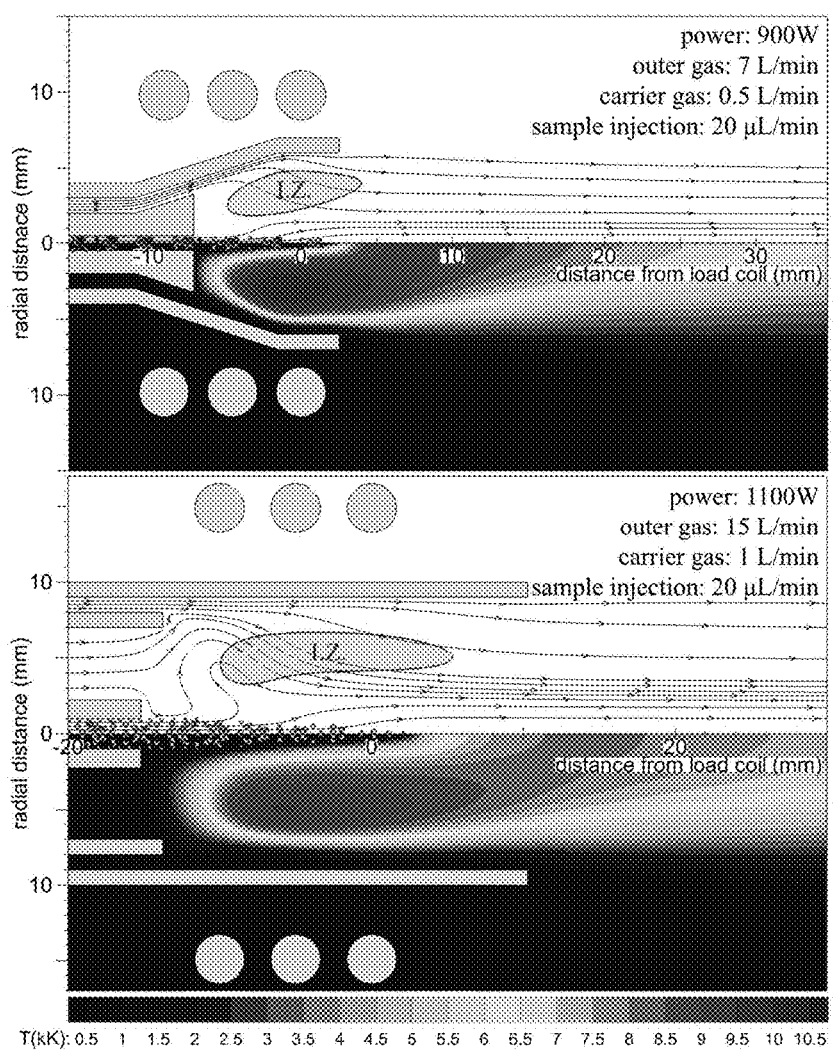

FIG. 15A shows computer-simulated streamlines (top), temperature (bottom), and aerosol (orange dots) distribution inside the new torch. The aerosol is composed of 5 µm water droplets. Power induction zones (I.Z.) are determined based on 1/e maximum current density inside the plasma.

FIG. 15B shows computer-simulated streamlines (top), temperature (bottom), and aerosol (orange dots) distribution inside the Fassel torch. The aerosol is composed of 5 µm water droplets. Power induction zones (I.Z.) are determined based on 1/e maximum current density inside the plasma.

Figures 16A, 16B:
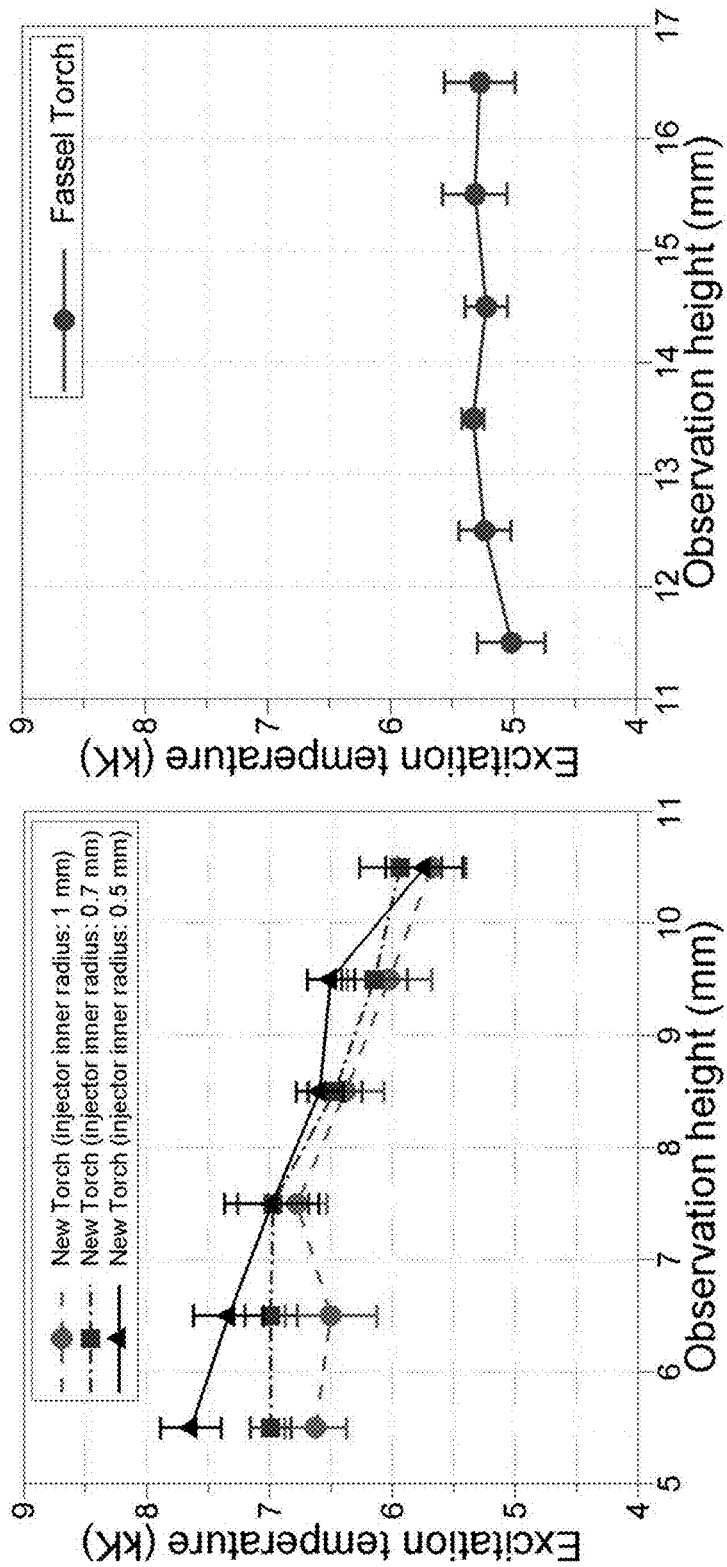

FIG. 16A shows variation of Fe excitation temperature against observation height after the load coil for the new torch.

FIG. 16B shows variation of Fe excitation temperature against observation height after the load coil for the Fassel torch.

Figures 17A, 17B:
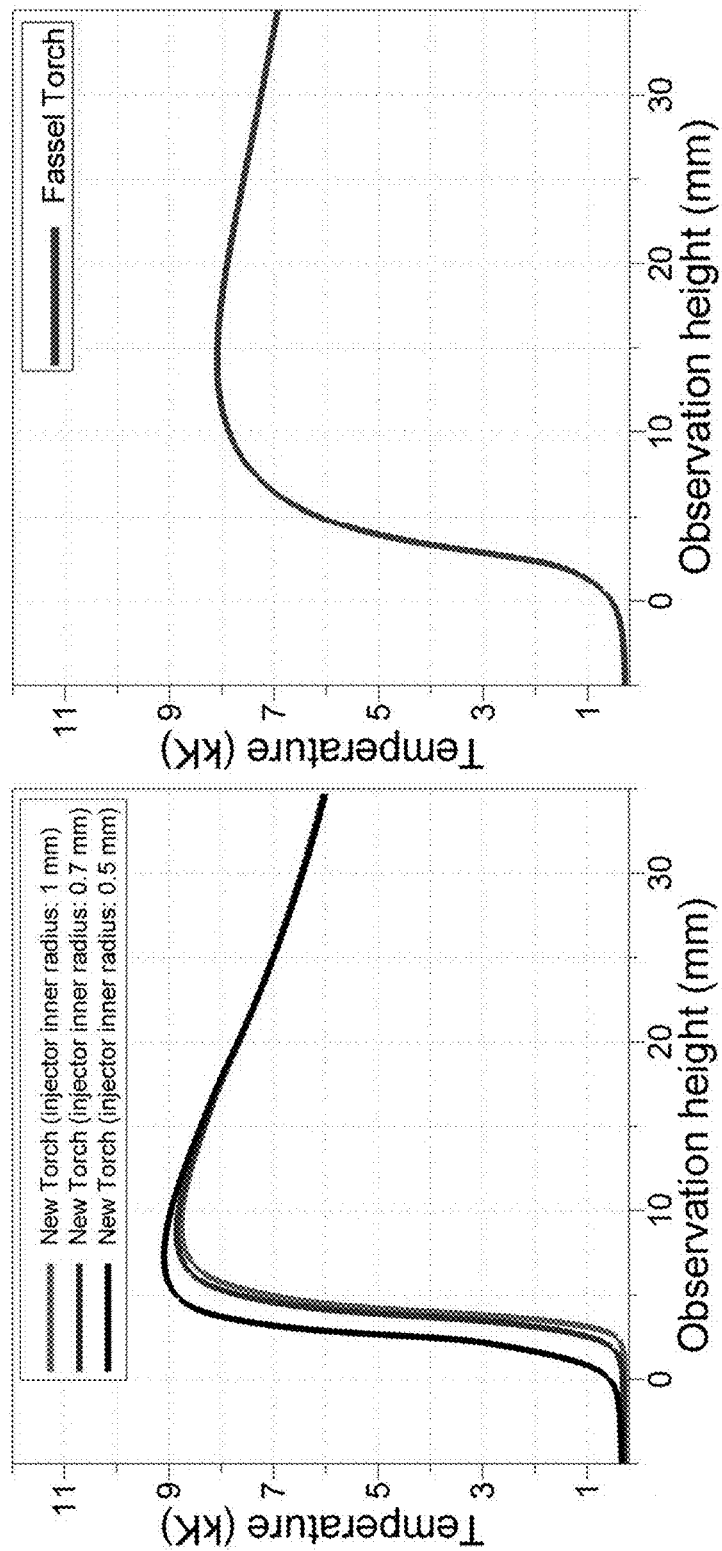

FIG. 17A shows computer-simulated variation of temperature against observation height after the load coil for the new torch.

FIG. 17B shows computer-simulated variation of temperature against observation height after the load coil for the Fassel torch.

Figures 18A, 18B:
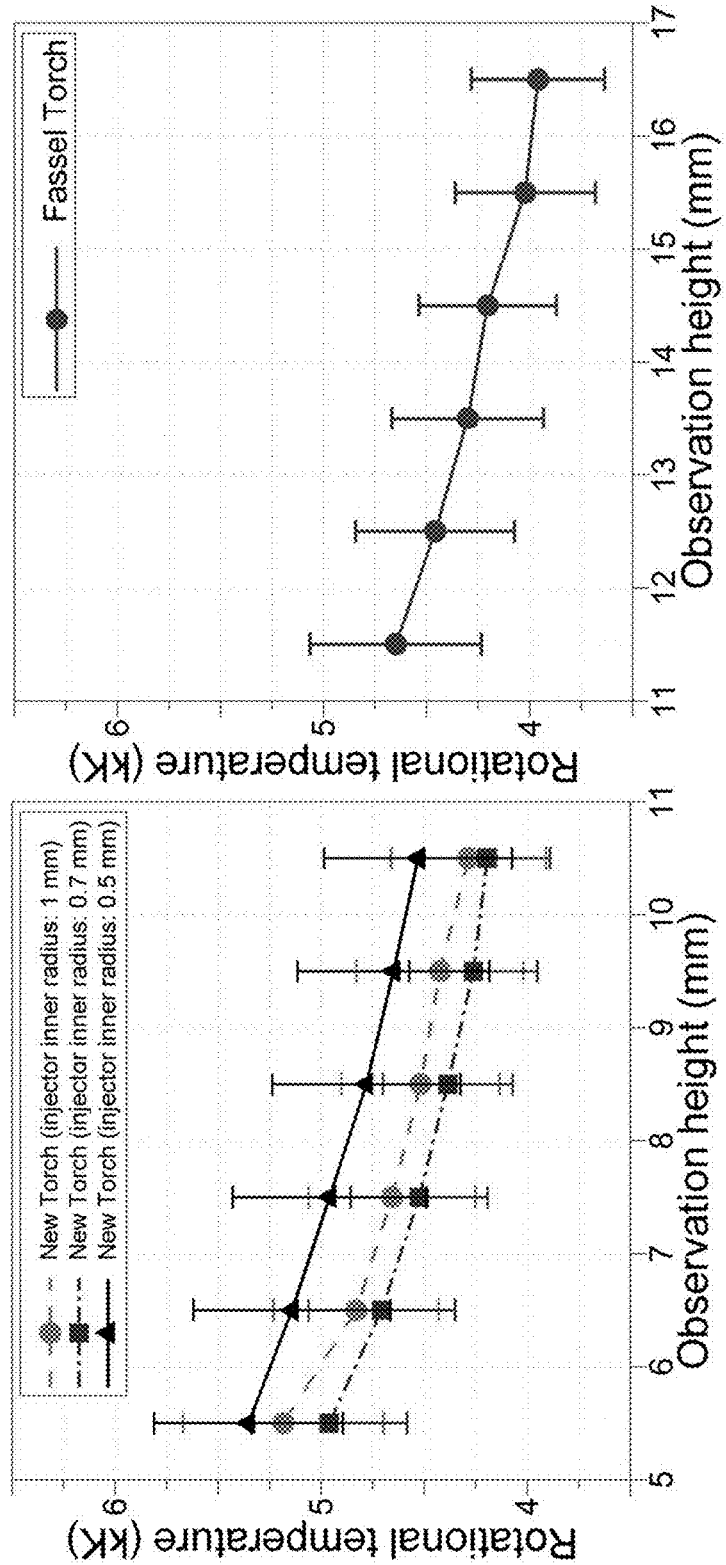

FIG. 18A shows variation of OH rotational temperature against observation height after the load coil for the new torch.

FIG. 18B shows variation of OH rotational temperature against observation height after the load coil for the Fassel torch.

Figures 19A, 19B:
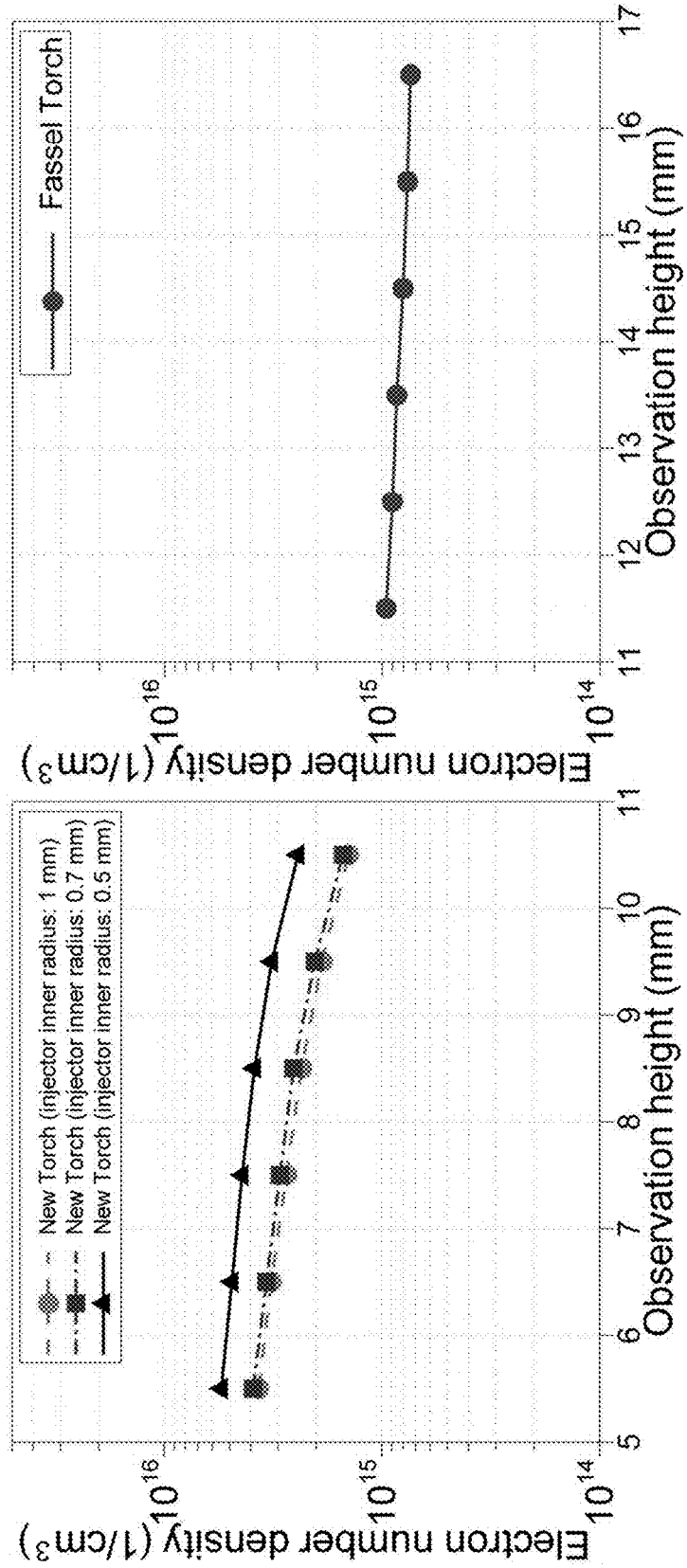

FIG. 19A shows variation of electron number density against observation height after the load coil for the new torch.

FIG. 19B shows variation of electron number density against observation height after the load coil for the Fassel torch.

Figure 20A:
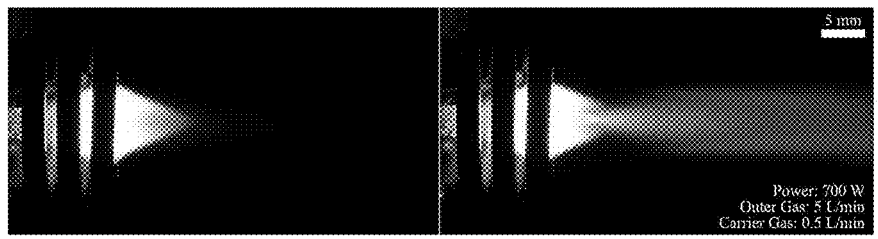

FIG. 20A shows condition of plasma in the new torch.

Figure 20B:
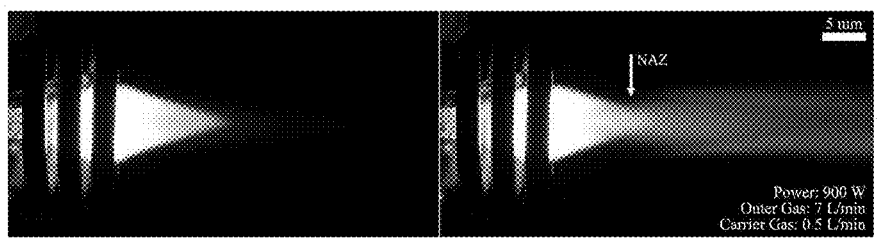

FIG. 20B shows condition of plasma in the new torch.

Figure 20C:
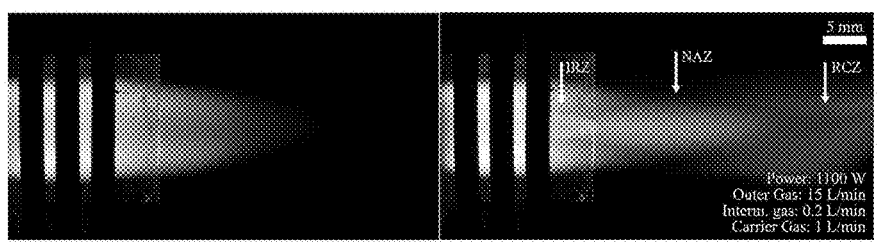

FIG. 20C shows condition of plasma in the Fassel torch.

Figure 20D:
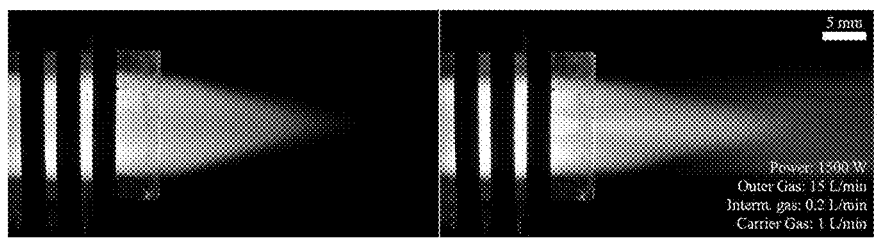

FIG. 20D shows condition of plasma in the Fassel torch.

Figures 21A, 21B:
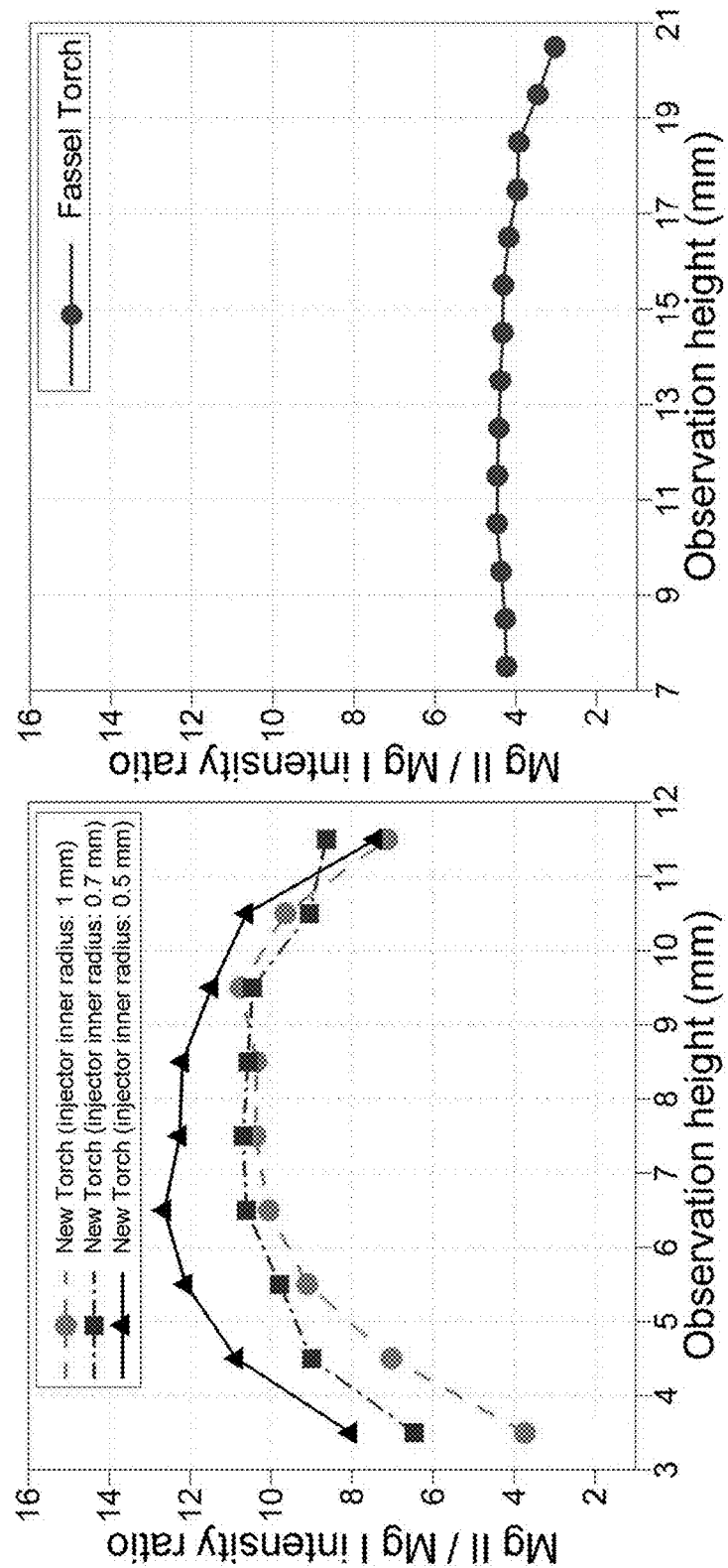

FIG. 21A shows variation of plasma robustness (Mg II/Mg I line intensity) against observation height after the load coil for the new torch.

FIG. 21B shows variation of plasma robustness (Mg II/Mg I line intensity) against observation height after the load coil for the Fassel torch.

Figures 22A, 22B:
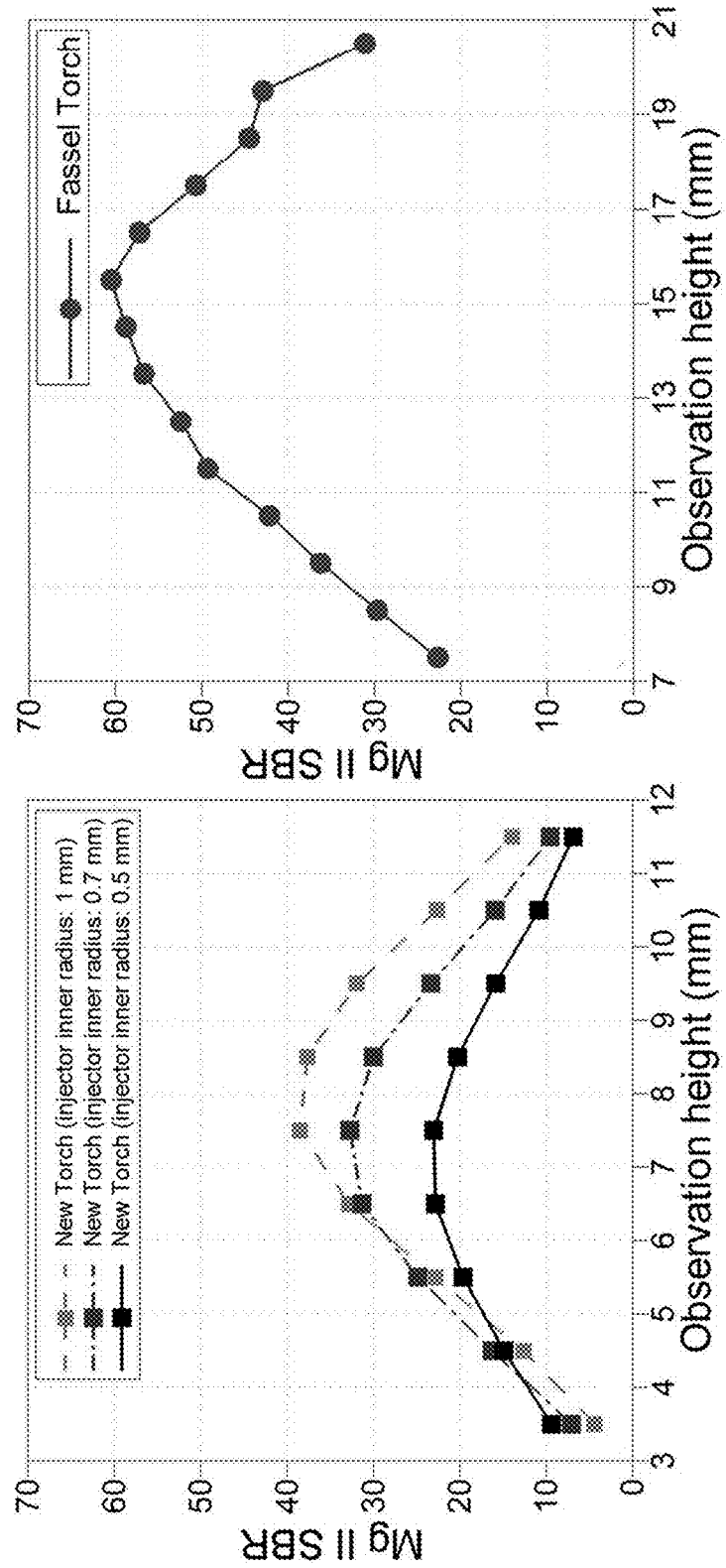

FIG. 22A shows variation of SBR for the Mg II 279.5528 nm line against observation height after the load coil for the new torch.

FIG. 22B shows variation of SBR for the Mg II 279.5528 nm line against observation height after the load coil for the Fassel torch.

Figures 23A, 23B:
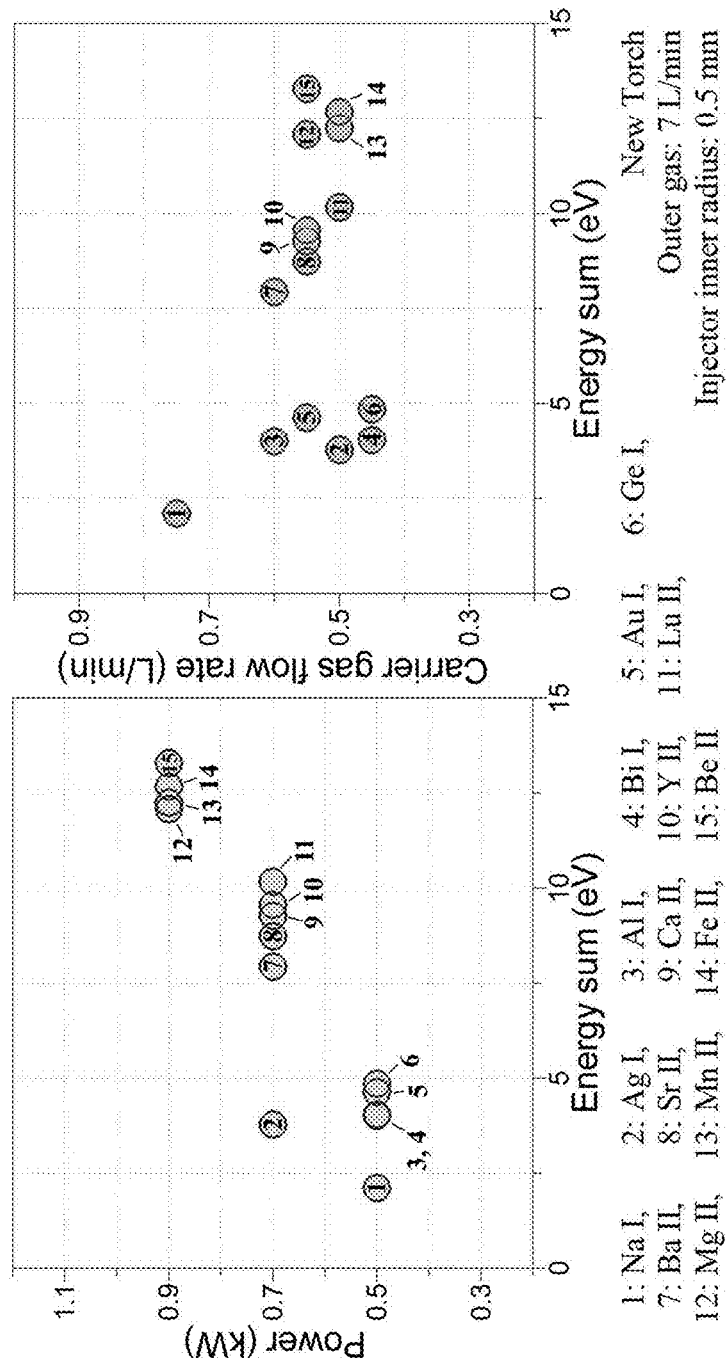

FIG. 23A shows effect of energy sum (i.e., sum of ionization and/or excitation energies) of spectral lines on optimum power of the new torch.

FIG. 23B shows effect of energy sum (i.e., sum of ionization and/or excitation energies) of spectral lines on optimum carrier gas of the new torch.

Figures 24A, 24B:
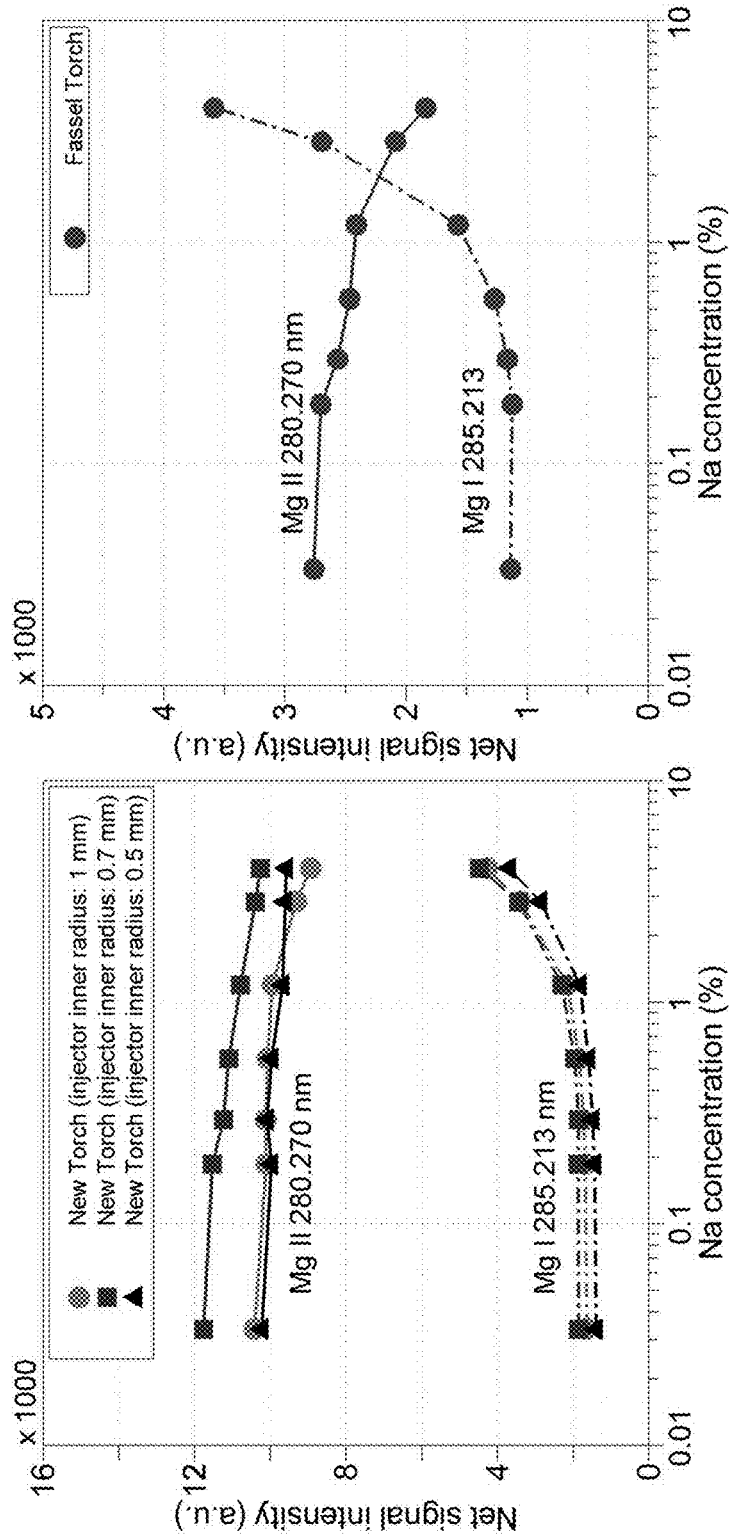

FIG. 24A shows effect of Na concentration (in 2% HNO3 solution) on net signal intensity of Mg II and Mg I lines for the new torches at optimized observation height and carrier gas flow rate.

FIG. 24B shows effect of Na concentration (in 2% HNO3 solution) on net signal intensity of Mg II and Mg I lines for the Fassel torches at optimized observation height and carrier gas flow rate.

Figure 25:
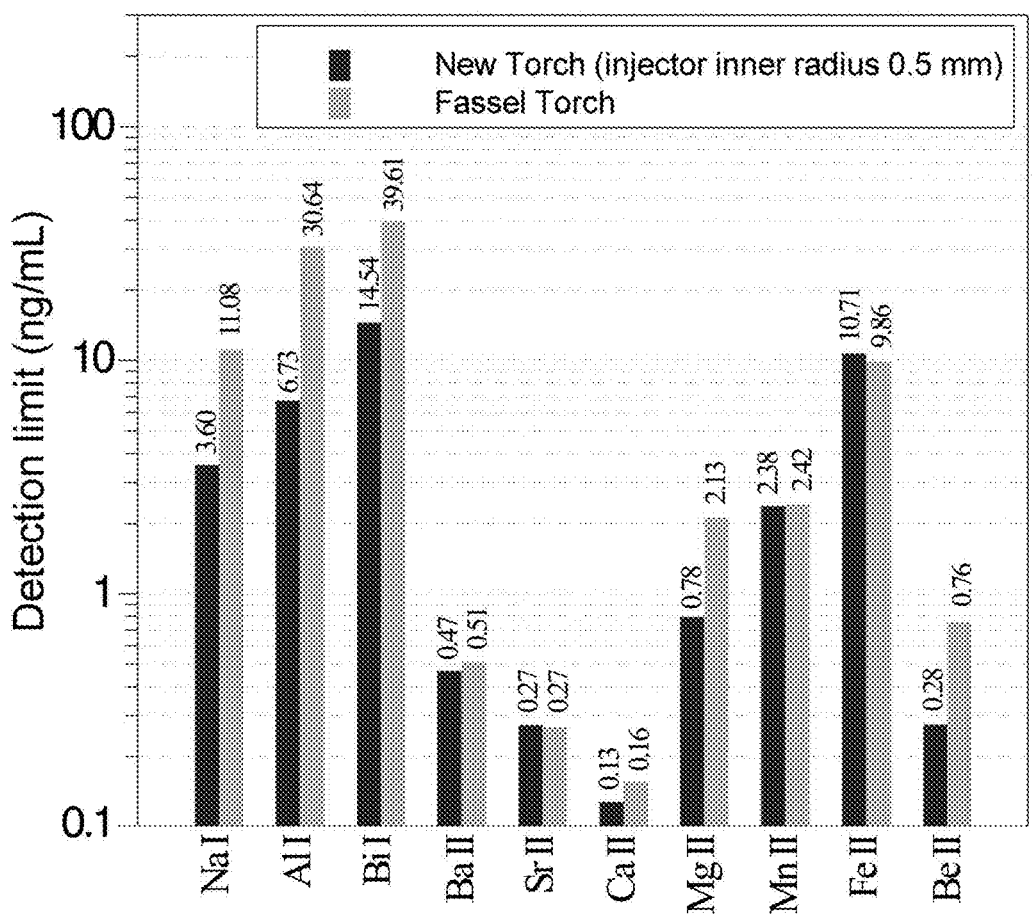

FIG. 25 shows detection limits for multi-element analysis with the new and Fassel torches. The spectral lines are sorted in the order of increasing energy sum (i.e., sum of ionization and/or excitation energies) from Na I to Be II.

FIG. 26A Shows a simulation of the effect of the conical ratio of 0.185 on flow pattern, magnetic field, temperature, and position of the plasma inside the new torch. Power, outer gas, and carrier gas are set to 1000 W, 8 L/min, and 1 L/min, respectively. The power induction zone (I.Z.) inside the plasma is determined based on 1/e maximum current density.

FIG. 26B Shows a simulation of the effect of the conical ratio of 0.318 on flow pattern, magnetic field, temperature, and position of the plasma inside the new torch. Power, outer gas, and carrier gas are set to 1000 W, 8 L/min, and 1 L/min, respectively. The power induction zone (I.Z.) inside the plasma is determined based on 1/e maximum current density.

FIG. 26C Shows a simulation of the effect of the conical ratio of 0.447 on flow pattern, magnetic field, temperature, and position of the plasma inside the new torch. Power, outer gas, and carrier gas are set to 1000 W, 8 L/min, and 1 L/min, respectively. The power induction zone (I.Z.) inside the plasma is determined based on 1/e maximum current density.

FIG. 26D Shows a simulation of the effect of the conical ratio of 0.578 on flow pattern, magnetic field, temperature, and position of the plasma inside the new torch. Power, outer gas, and carrier gas are set to 1000 W, 8 L/min, and 1 L/min, respectively. The power induction zone (I.Z.) inside the plasma is determined based on 1/e maximum current density.

Figure 13A:
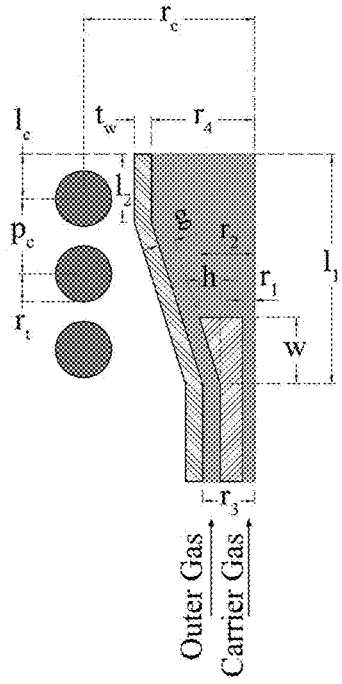
FIG. 13A shows geometrical parameters of the new torch.
Figure 13B:
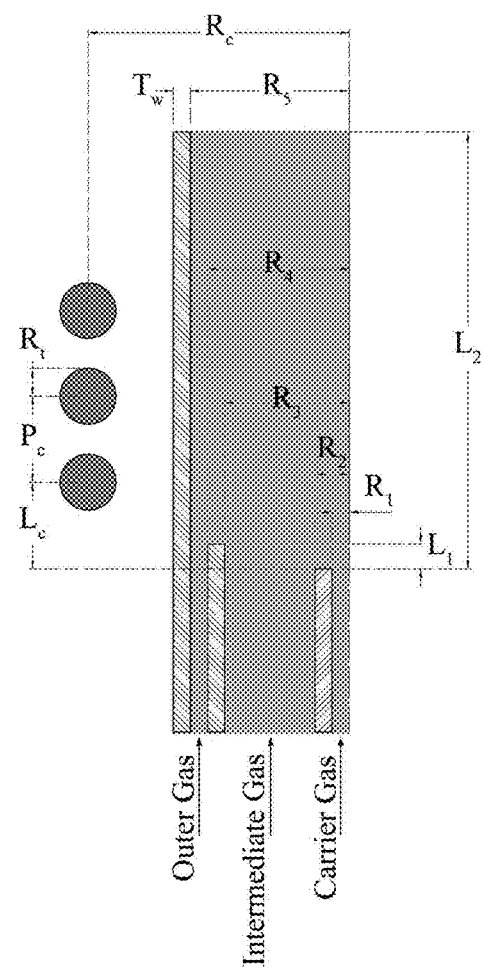
FIG. 13B shows a conventional Fassel torch.
Figure 27:
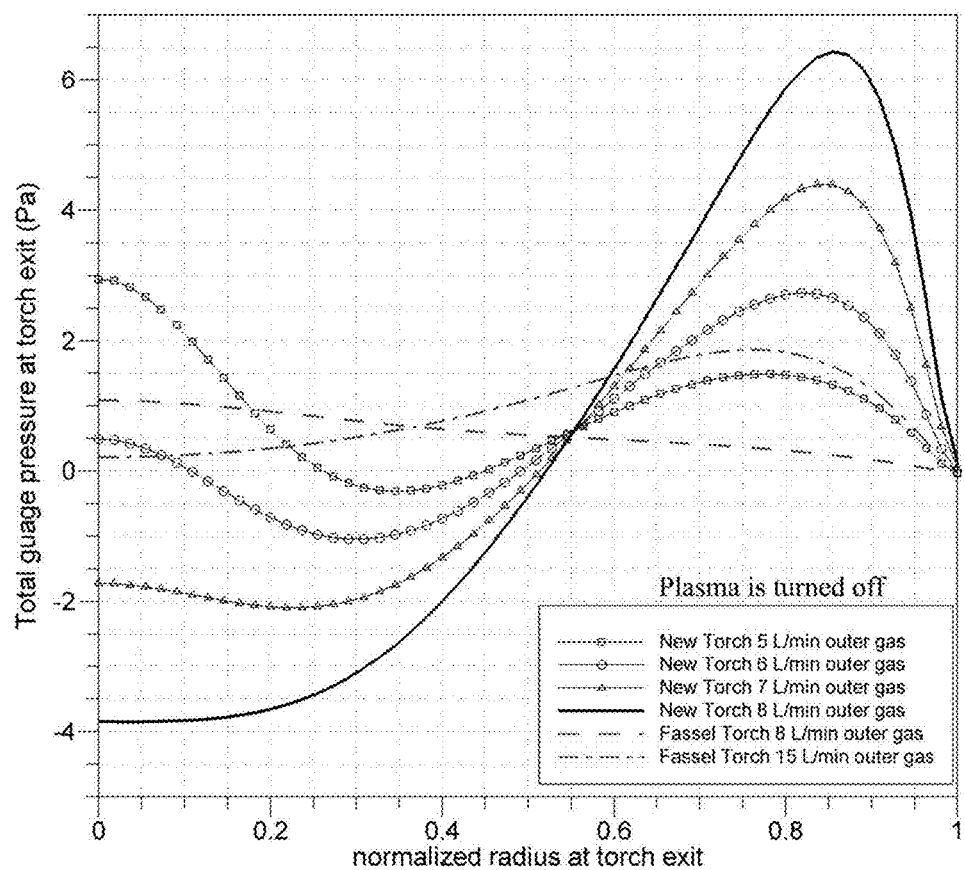

FIG. 27 shows the computer-simulated variation of the total gauge pressure along the torch radius (normalized with $r_4$ for the new torch and $R_5$ for the Fassel torch described in FIGS. 13A and 13B) for various outer gas flow rates.

Figure 28A:
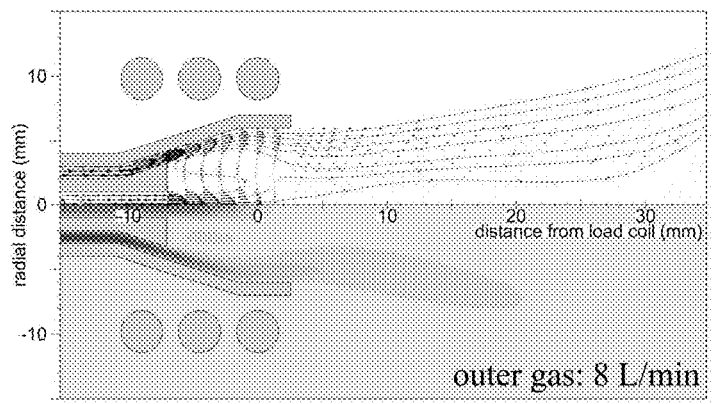

FIG. 28A shows the computer-simulated streamlines, velocity vectors (top) and contour of velocity (bottom) inside the new torch for 8 L/min outer gas flow.

Figure 28B:
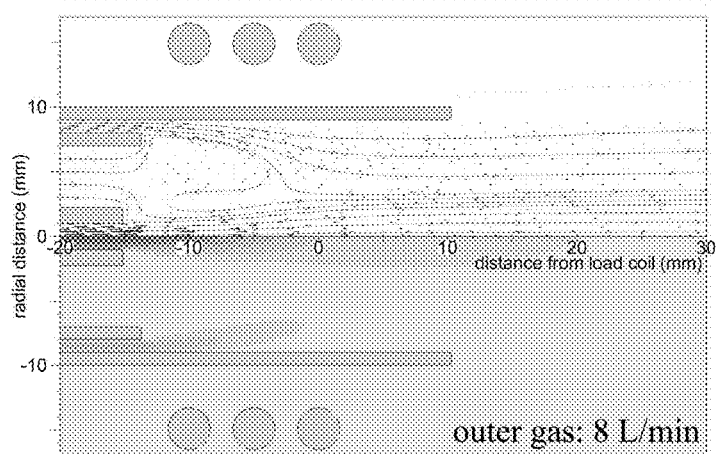

FIG. 28B shows the computer-simulated streamlines, velocity vectors (top) and contour of velocity (bottom) inside the Fassel torch for 8 L/min outer gas flow.

Figure 28C:
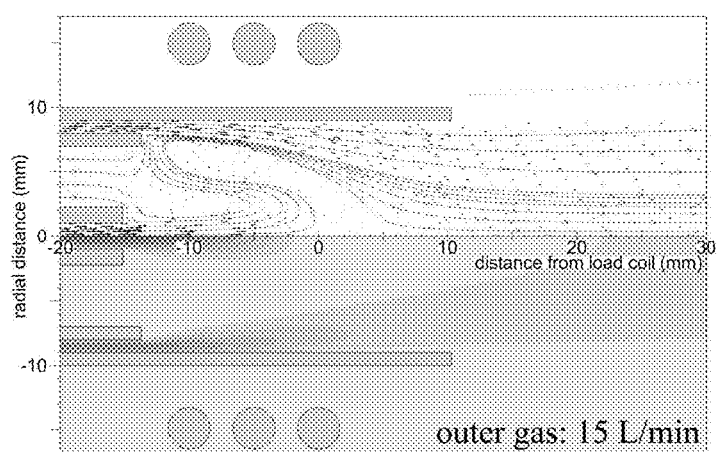

FIG. 28C shows the computer-simulated streamlines, velocity vectors (top) and contour of velocity (bottom) inside the Fassel torch for 15 L/min outer gas flow.

Figure 29A:
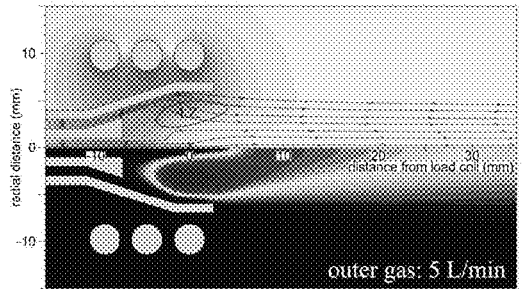

FIG. 29A shows computer-simulated temperature (bottom), magnetic flux density (top) and streamlines inside the new torch for 5 L/min outer gas flow.

Figure 29B:
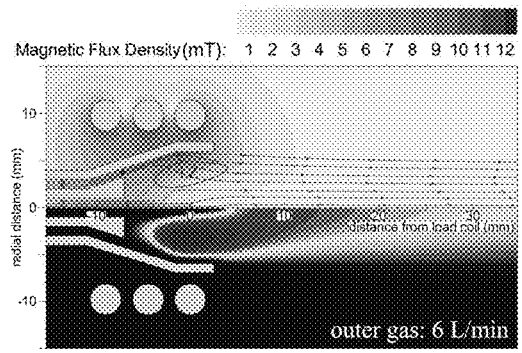

FIG. 29B shows computer-simulated temperature (bottom), magnetic flux density (top) and streamlines inside the new torch for 6 L/min outer gas flow.

Figure 29C:
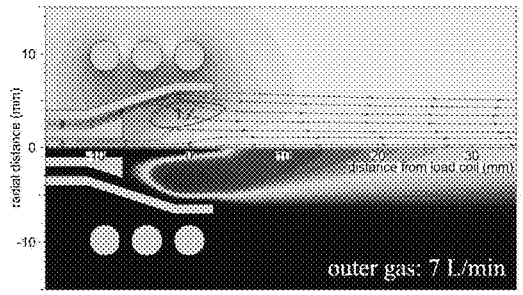

FIG. 29C shows computer-simulated temperature (bottom), magnetic flux density (top) and streamlines inside the new torch for 7 L/min outer gas flow.

Figure 29D:
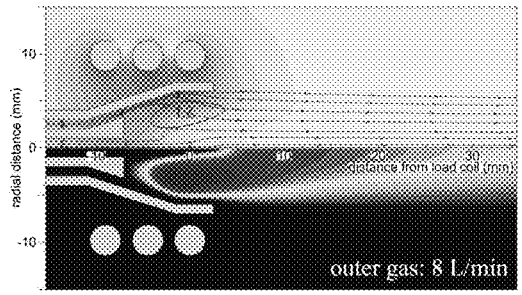

FIG. 29D shows computer-simulated temperature (bottom), magnetic flux density (top) and streamlines inside the new torch for 8 L/min outer gas flow.

Figure 29E:
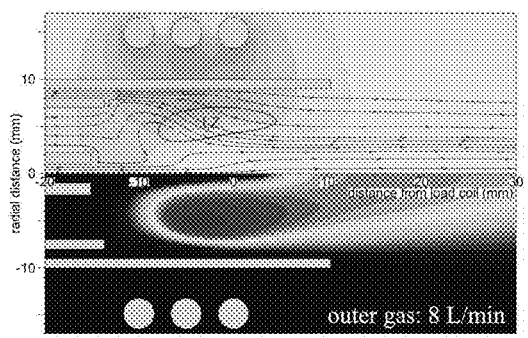

FIG. 29E shows computer-simulated temperature (bottom), magnetic flux density (top) and streamlines inside the Fassel torch for 8 L/min outer gas flow.

Figure 29F:
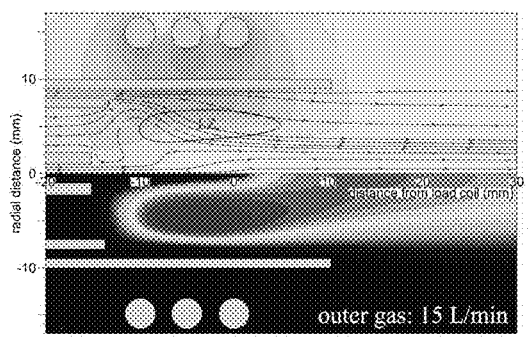

FIG. 29F shows computer-simulated temperature (bottom), magnetic flux density (top) and streamlines inside the Fassel torch for 15 L/min outer gas flow.

Figure 30A:
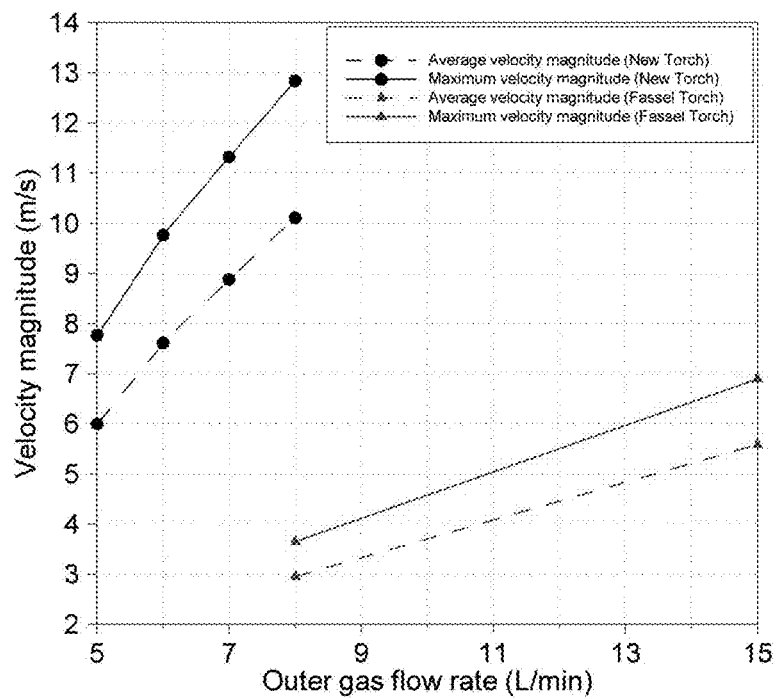

FIG. 30A shows the computer-simulated variation of outer gas velocity at the point of discharge between the outer tube and injector/intermediate tube for the new/Fassel torches.

Figure 30B:
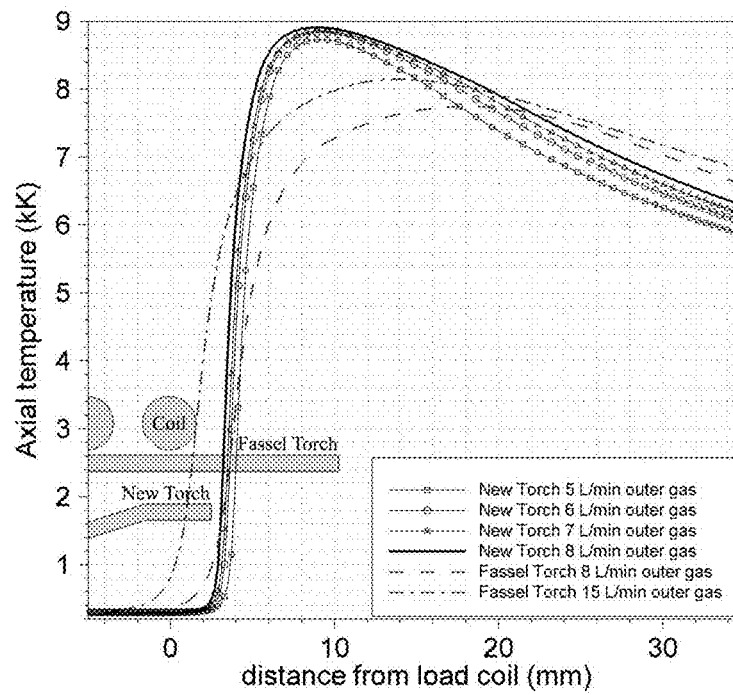

FIG. 30B shows variation of temperature along the central axis of the new and Fassel torches. The power, intermediate gas (only for the Fassel torch), and carrier gas are set to 1000 W, 1.2 L/min, and 1 L/min, respectively. The extent of both torches are shown for better comparison.

Figure 31:
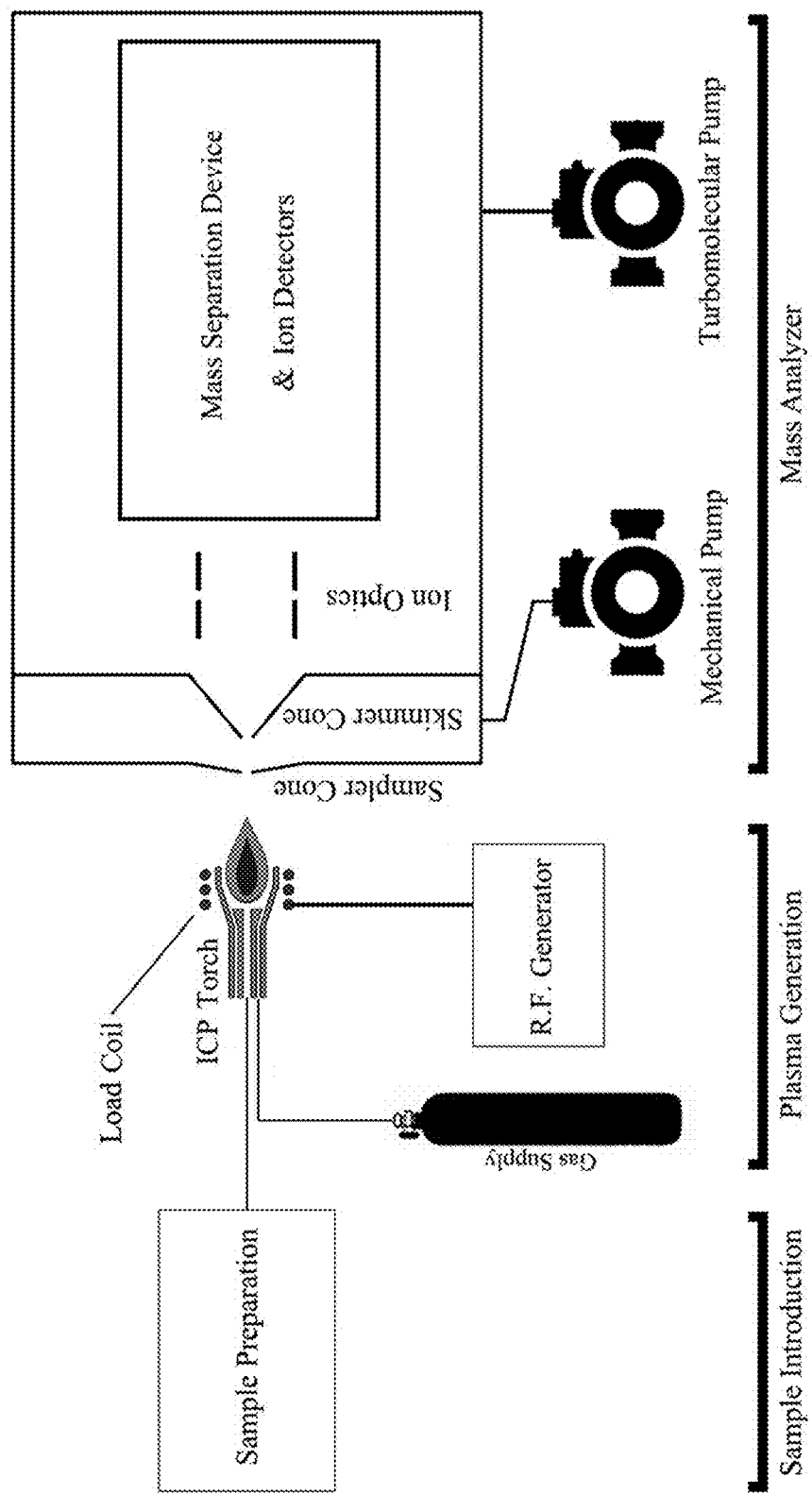

FIG. 31 is a diagram of a mass spectrometer incorporating a torch of the subject invention.

DESCRIPTION OF VARIOUS EMBODIMENTS

Figure 1:
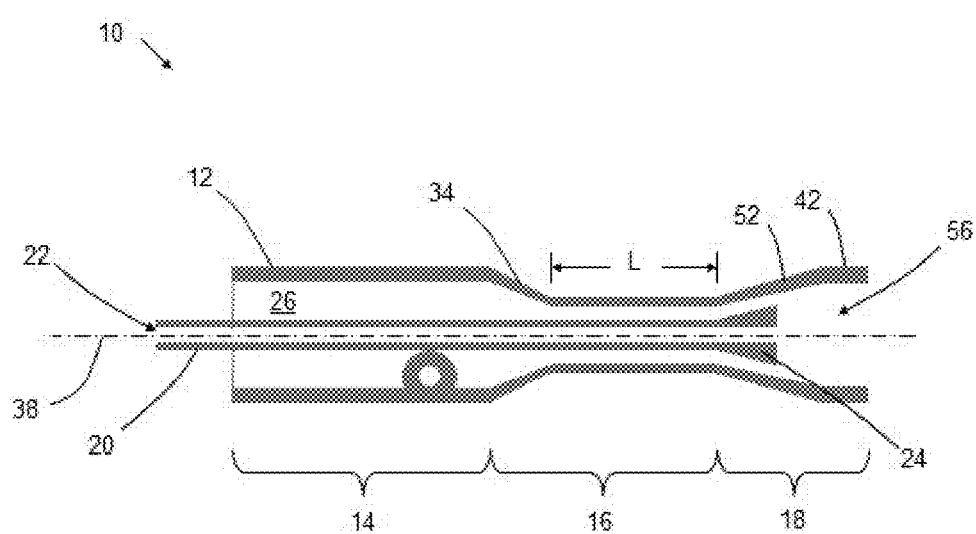
FIG. 1 is a view from one side of a torch in accordance with the present teachings.
Figure 2:
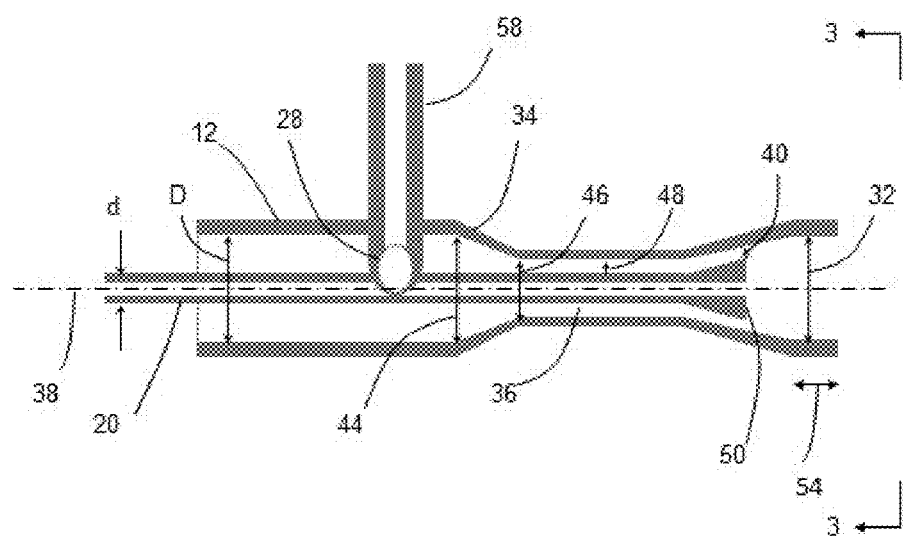
FIG. 2 is a view from another side of the torch of FIG. 1.
Figure 3:
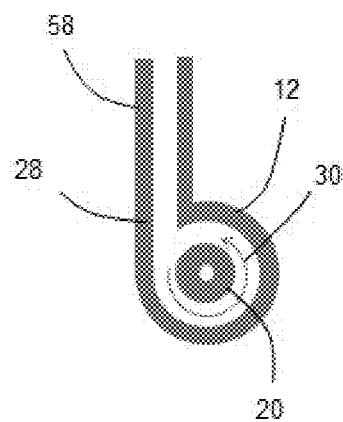
FIG. 3 is a view in the direction of arrows 3-3 of FIG. 2.

It should be understood that the phrase "a" or "an" used in conjunction with the present teachings with reference to various elements encompasses "one or more" or "at least one" unless the context clearly indicates otherwise. Reference is first made to FIG. 1, which shows a schematic representation of the plasma torch, generally indicated by reference number 10. The torch 10 comprises a torch tube 12, typically made of quartz glass, which can be conveniently characterized by three general sections along the axis 38. The first sections of the torch tube 12 can be defined as a support end 14, followed by an elongated neck 16 as the second section and the third section ending downstream with a conical end 18. Typically, the torch 10 comprises a gas inlet 28 that can be configured to connect to the torch tube 12 in a tangential arrangement located in the support end 14 as shown in FIG. 2. The torch 10 can also include an injector tube 20 that can be held in position within the torch tube 12 so that the tubes (12,20) are in concentric alignment as shown in FIG. 3. The injector tube 20 can be configured with an injector inlet end 22 for receiving a sample from various sources and an injector conical end 24 where the sample can pass through into the plasma. Within the space between the concentric tubes (12,20) an annular ring shaped geometry extends from the support end 14 to the conical end 18 so that an annular channel 26 can be formed along the axis 38. In general, the annular radius of the annular channel 26 can be characterized by the difference between the inner diameter D of the torch tube 12 and the outside diameter d of the injector tube 20. For brevity, the terms gap and annular radius can be used interchangeably. In various embodiments, as illustrated in FIG. 1 and FIG. 2, the configuration of the annular channel 26 varies through the sections (14,16,18) along the axis 38 so that the corresponding gap also varies. The nature of the variable annular channel 26 will be described below.

Accordingly, in various embodiments, the elongated neck 16 of the torch tube 12 comprises a tapered portion that defines an angular accelerator 34 followed with a straight portion of length L to define an elongated annular channel 36. As illustrated in FIG. 2, the angular accelerator 34 has an upstream end that is wider with a diameter 44 at the support end 14 and tappers to a narrower diameter 46. Consequently, the annular channel 26 in the angular accelerator 34 resembles a tapered conical ring. The narrower diameter 46 continues along the length L so that the elongated annular channel 36 can be defined by a gap 48 that is narrower than the gap of the annular channel 26 at the support end 14.

Figure 4:
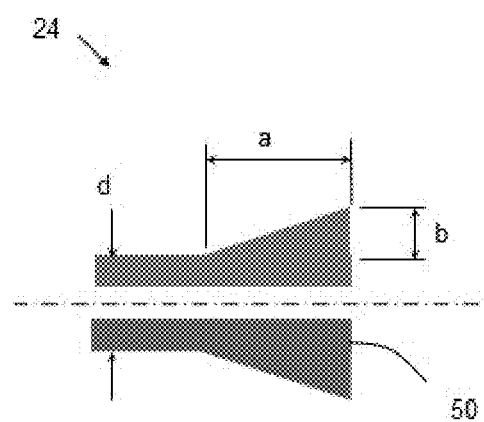
FIG. 4 is a view of the injector conical end 24 of the torch of FIG. 1, on a large scale.
Figure 7:
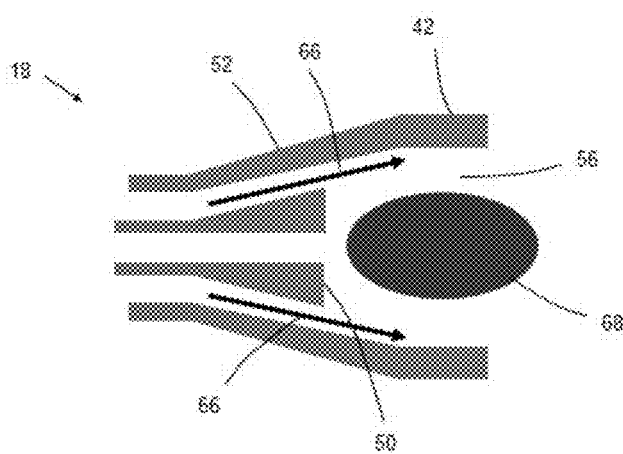
FIG. 7 is a view of the conical end 18 of the torch of FIG. 1, on a large scale.

The embodiments of the conical end 18 of the torch tube 12 and the injector conical end 24 of the injector tube 20 will now be described. With reference to FIG. 4, the injector conical end 24 comprises a cone shape geometry where the diameter d of the injector tube 20 increases over a length a to form a cone with a base 50 having a partial annular radius b. The cone shaped geometry of the injector conical end 24 is typically characterized by a cone angle, and in accordance with the present teachings, the cone angle can be represented by the cone ratio b/a. Furthermore, the configuration of the conical end 18 of the torch tube 12 has a corresponding geometry where the diameter D is increased to form a conical taper portion 52 that is parallel with the cone shape of the injector conical end 24. In various embodiments, the conical taper portion 52 extends beyond the base 50 as shown in FIG. 7. Consequently, the annular channel 26 with a conical gap 40 can be formed between the injector conical end 24 and the conical end 18 of the torch tube 12 as shown in FIG. 2. In this configuration, the dimensions of the gap 48 along the elongated annular channel 36 and subsequently the conical gap 40 between the conical ends (18, 24) can be selected so that the axial velocity of a gas passing from the support end 14 to the conical end 18 can experience acceleration.

In various embodiments, the conical end 18 can also be configured with an axially straight portion 42 that extends from the conical taper portion 52 as shown in FIG. 1 and FIG. 2. Generally, the axially straight portion 42 can be described as being a cylinder with a diameter 32 of length 54. The cylindrical dimensions (32, 54) can be selected so that the region bounded between the axially straight portion 42 and the base 50 of the injector conical end 24 forms a cavity 56 suitable for confining the plasma.

Figure 5:
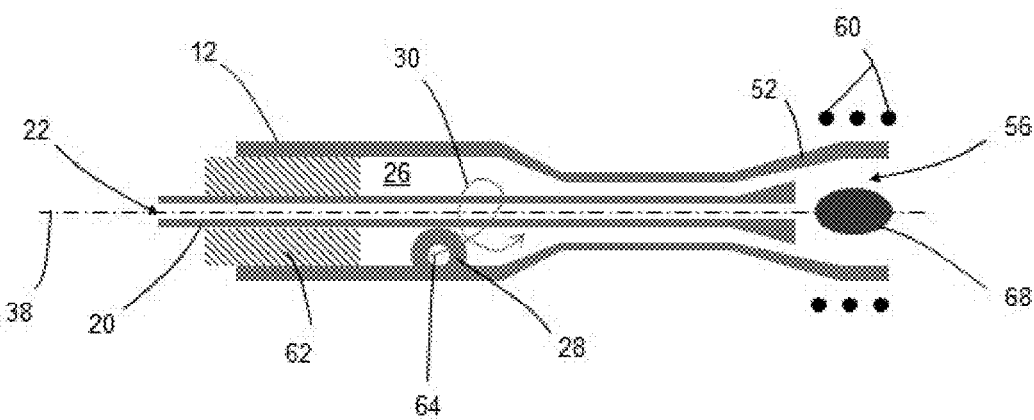
FIG. 5 is similar view of the torch of FIG. 1, showing the orientation of the torch in use.

In use, the torch 10 is typically held upstream at the support end 14 by a torch holder 62 so that the conical end 18 can be position within an conventional RF load coil 60 as shown in FIG. 5. The holder 62 also functions to hold and align the injector tube 20 within the torch tube 12 and to close the space there between. In various embodiments for example, the torch tube 12 can be configured to close in at or around the injector tube 20 by alternative means while permitting access to the injector inlet end 22. Consequently, the torch 10 can be held by any other means as required.

Figure 6:
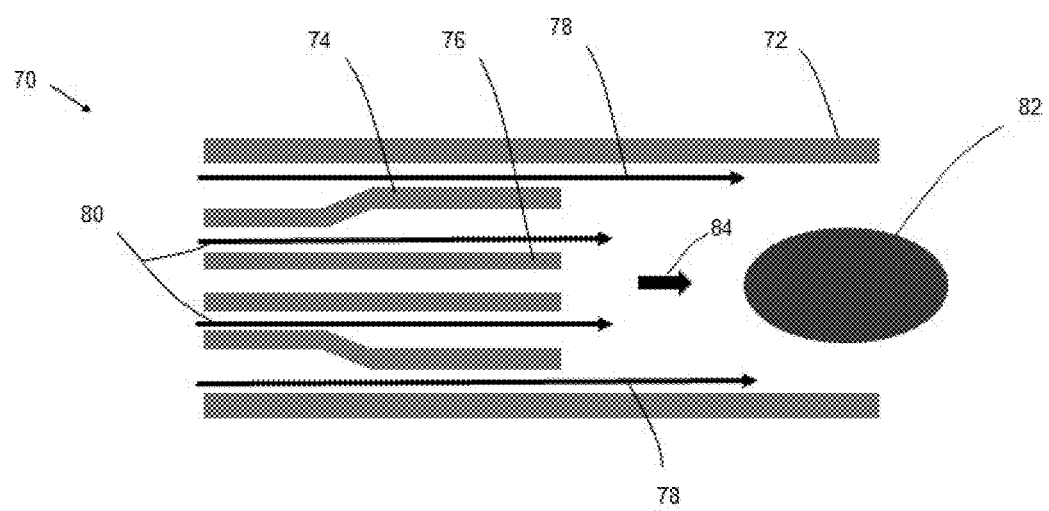
FIG. 6 is a schematic view of a conventional torch.

A typical conventional argon ICP torch 70, shown in FIG. 6, consist of an assembly of two concentric quartz tubes, an outer tube 72 and an middle tube 74. The conventional torch 70 also utilizes an inner tube 76 that serves to deliver the sample to the plasma ball generally indicated at 82. The conventional torch 70 requires a flow of 'outer gas' and a flow of 'intermediate gas' represented by the arrows 78 and 80 respectively. Even with a high temperature material like quartz, the heat from the plasma ball 82 can cause severe damage leading to a number of undesirable effects, such as devitrification. To prevent this, the conventional torch 70 uses a high argon flow rate for the outer gas 78 (about 16 l/m) passed between the outer tube 72 and the middle tube 74. The outer gas 78 confines the plasma ball 82 and to keep the plasma ball 82 and the heat generated within the plasma ball 82 away from the quartz wall of the outer tube 72. In addition, the intermediate gas 80 flowing between the middle tube 74 and the inner tube 76, at a argon flow rate of about 1 l/m, is required to position the plasma ball 82 forward 84 away from the middle tube 74 and the inner tube 76.

However, in accordance with the present teaching, the torch 10 operates with a single gas flow for generating the plasma ball 68 and for positioning the plasma ball 68 away from the torch surfaces. The flow of gas 64 can be supplied to the gas inlet 28 by various means so that the gas 64 passes into the support end 14 tangentially around the annular channel 26, as shown in FIG. 5. The streamline 30 in the annular channel 26 indicates that the gas flow is under a rotational force. Since the support end 14 is closed around the holder 62, or closed by other means, the gas continues with its rotational flow downstream that resembles a swirling spiral. In particular, the trajectory of the gas flow within the spiral path can be characterized in part by its velocity components, namely an angular velocity and an axial velocity. As the flow of gas rotates around the annular channel 26 and pass through the angular accelerator 34, the narrowing diameter (from 44 to 46) of the torch tube 12 has the effect of reducing the gas flow's rotational radius while increasing the flow's axial velocity. Thus, according to the law of conservation of momentum, the angular velocity of the gas necessarily increases as the gas flow pass through the angular accelerator 34. Consequently, the swirling gas flowing through the narrower 48 elongated annular channel 36 will have an increase in both of its axial velocity and its angular velocity.

Figure 8:
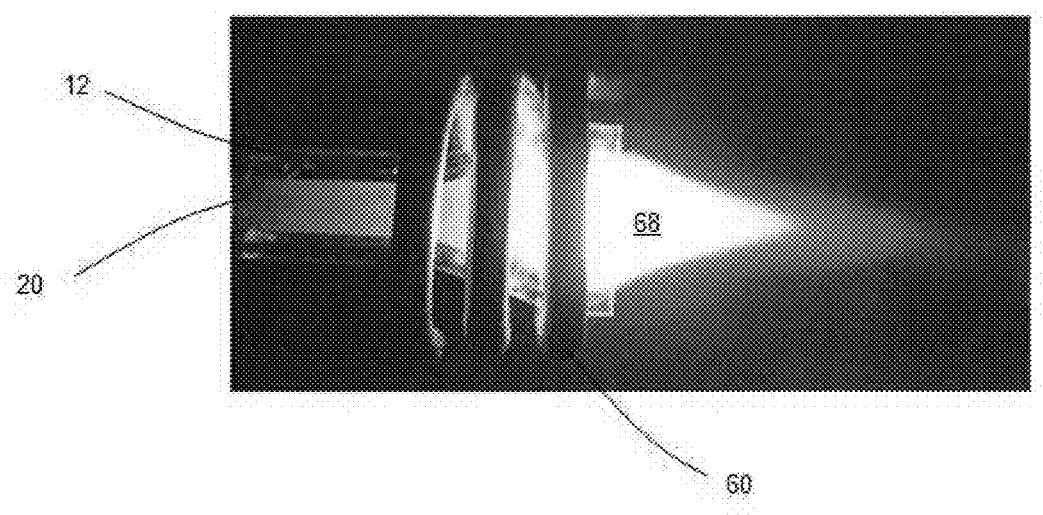
FIG. 8 is an image of the plasma ball generated within the torch of FIG. 1.

Subsequently, as the gas passes into the cavity 56 of the torch 10 the increased angular velocity of the swirl will have the effect of maintaining the swirl within the cavity. Also, as the accelerated gas flows through the conical gap 40, the axial component of the accelerated gas can flow parallel to the conical taper portion 52. This accelerated axial flow, generally indicated by the arrows 66 in FIG. 7, has the effect of encouraging the flow of gas to follow along the torch tube 12 surface thus forming a cooling barrier for the cavity 56. Although the accelerated gas flow parallel to the conical taper portion 52 can provide sufficient cooling between the plasma ball and the surface of the torch tube 12, it is recognized that the structure of the gas flow, such as the trajectory of the flow into the cavity, can affect the location of the plasma ball. Consequently, the conical ratio b/a and the dimension of the conical gap 40 can be selected so that the gas flow's axial velocity is maximized to provide a sufficient cooling barrier to prevent devitrification of the quartz while the trajectory of the gas flow remains parallel to the surface of the torch tube 12 in order to maintain the plasma ball 68 within the cavity 56. In various embodiments, for example, the conical ratio b/a can be in the range between 0.1 and 1.5, and the conical gap 40 can be about 1 mm. In some instances, the conical ratio b/a can be in the range between 0.3 and 0.6. As an example, a torch 10 of the present teaching was configured with a straight portion 42 diameter 32 of 12 mm, a conical ratio b/a of about 0.3 and a conical gap 40 of about 1 mm. With this configuration, a plasma ball 68 was sustained with an argon gas flow of about 4 l/m at a RF power of about 900 W without any thermal damage to the quartz tube, as shown in FIG. 8.

While the present teachings are described in conjunction with various embodiments, it is not intended that the present teachings be limited to such embodiments. On the contrary, the present teachings encompass various alternatives, modifications, and equivalents, as will be appreciated by those of skill in the art. For example, the present applicants recognize that the gas inlet 28 can be configured to include a gas tube 58 where the supply of argon can be conveniently delivered using conventional fittings. Alternatively, the holder 62 can be configured to introduce a supply of argon gas to the support end 14 with a rotational force so that the gas passes in to the annular channel 26 with an existing rotation. Consequently, the gas inlet 28 can be omitted with this arrangement.

Furthermore, although the diameter d of the injector tube is shown to remain unchanged until the injector conical end 24, in some instances, the diameter d can be varied along the axis as required. For example, in order to accommodate a greater acceleration effect through the angular accelerator 34, the diameter d of the injector tube can be narrower through the elongated neck 16. In this configuration, the diameter 46 of the elongated annular channel 36 can be further narrowed while maintaining an optimum gap 48.

In some cases, the torch tube 12 may have a diameter at or between 2 mm and 20 mm, between 2 mm and 12 mm, between 4 mm and 16 mm, between 4 and 12 mm, between 6 mm and 12 mm, between 8 and 10 mm, less than 20 mm, less than 16 mm, less than 12 mm, less than 10 mm, less than 8 mm, less than 6 mm, or less than 4 mm. In certain aspects, the torch may not have an angular accelerator 34 and elongated annular channel, such that there are not separate elements 14 and 16.

In some cases, the conical gap 40 may be at or between 0.1 to 3 mm, 0.5 and 2 mm, or about 1 mm.

In some cases, the torch 10 can be positioned adjacent to an energy source other than an RF load coil 60 for generating the plasma ball, such as a microwave energy source.

In some cases, Helium, Nitrogen, Air, Oxygen, or Hydrogen may be used as an alternative, or in addition, to Argon.

In some cases the torch, its injector, or both, may be made from a refractory material other than quatz. For example, the torch may include one or more of Alumina, Boron Nitride, Silicone Nitride, Silicone Carbide, Zirconia, Yttria, Ceria, Beryllium Oxide.

As described in the examples below, a range of dimensions are suitable for the torch described herein. For example, the dimensions of the torch described herein about the dimensions shown in FIG. 13A, such as within the range of +/−30%, +/−20%, +/−10%, or +/−5% of the dimensions shown for the new torch in FIG. 13A. For example, the injector inner radius may be between 0.25 and 1 mm, between 0.25 and 0.7 mm, between 0.25 and 0.5 mm, between 0.5 and 1 mm, between 0.7 and 1 mm, between 0.5 and 0.7 mm, 1 mm or less, 0.7 mm or less, or 0.5 mm or less. In certain aspects, the radius of the load coil may be scaled with the radius of the torch output. For example, the ratio of the load coil radius to the plasma outlet radius may be about 5/3, such as between 1.25 and 2, between 1.4 and 1.85 or between 1.55 and 1.75.

As described further herein, a range of conical ratios may be used. For example, a conical ratio of 0.1 to 4, 0.1 to 3, 0.1 to 1.5, 0.1 to 1, 0.15 to 0.6, 0.2 to 0.4, greater than 0.1, or greater than 0.3, may be used. As shown in FIG. 28, a range of conical ratios provide benefits described herein. In some embodiments, the shape of the long edge of the cone may be straight. In some embodiments, the injector end 24 and/or taper portion 52 shown in FIG. 1 may be convex or concave, for example describing a bell shape.

As compared to the traditional torches (e.g., the Fassel Torch), the subject torch may have a smaller torch diameter, higher gas velocity, and/or a smaller load coil. The subject torch may have a cone enclosing the plasma. The outer gas may be introduced so as to form a gas swirl.

As compared to traditional torches (e.g., torches described in FIG. 10, such as the Fassel Torch shown in FIG. 9), the torch of the subject disclosure may provide improved performance. Such improvement may be measured when operating the new torch and Fassel torch under their respective optimized parameters, such power and/or gas flow rate. Alternatively, such improvement may be measured when operating the new torch a Fassel torch under the same parameters, such as the same or similar power and/or gas flow rate. Improved performance may include one or more of: higher temperature, higher signal measured by an elemental analyzer, reduced argon consumption, improved plasma stability, improved shielding of the torch body and/or lifetime of the torch. In certain aspects the new torch may provide the same or better performance when run at a lower power and/or gas flow rate as a Fassel torch.

For example, the subject torch may provide a decrease in gas consumption, such at least a 20% decrease, at least a 30% decrease, at least a 50% decrease, at least a 70% decrease, at least an 80% decrease, between 20% and 70% decrease, between 30% and 70% decrease, or between 50% and 70% decrease. Alternatively, or in addition, the subject torch may provide a decrease in energy consumption, such at least a 10% decrease, at least a 20% decrease, at least a 30% decrease, at least a 40% decrease, between 10% and 40% decrease, between 20% and 40% decrease, between a 20% and 70% decrease, or between 30% and 40% decrease. The subject torch may provide an increase in excitation temperature, such at least a 500K increase, at least a 1000K increase, at least a 2000K increase, between a 500K and 2000K increase, or between a 1000K and 1800 increase. The subject torch may provide an increase in rotational temperature, such at least a 500K increase, at least a 800K increase, at least a 1000K increase, between a 500K and 1500K increase, or between a 800K and 1400 increase. The subject torch may provide a high electron number density, such as a density that is at least 2 times higher, at least 3 times higher, at least 4 times higher, at least 5 times higher, between 2 and 8 times higher, between 4 and 6 times higher. The subject torch may provide a high robustness (e.g., Mg II to Mg 1 ratio), such as a robustness that is at least 1.5 times higher, at least 2 times higher, at least 3 times higher, between 1.5 and 4 times higher, between 2 and 4 times higher, between 2 and 5 times higher. The subject torch may reduce easily-ionizable elements (EIE) interferences.

Experimental

Design

An ICP torch for optical/mass spectrometry with a conical geometry as described herein can provide a reduction in gas and power consumption. The torch has been designed based on fluid flow patterns, heat transfer, plasma physics, and analytical performance. Computer simulations, capable of accounting for magneto-hydrodynamic effects, have been used to optimize torch geometry in the examples below. The result is a "conical" torch with up to 70% reduction in argon flow and more than 4 times power density compared with traditional "cylindrical" torches. Based on experimental measurements, these features lead to a stable plasma with 1000-1700K higher excitation/rotational temperature and a 5-fold increase in electron number density compared to common torches. Interferences from easily-ionizable elements (e.g., Na) are also observed to be minimized due to 3 times higher robustness (Mg II/Mg I ratio). Analytical parameters including detection limits for multi-element analysis may indicate comparable/better performance of the new torch in comparison with conventional torches.

Inductively coupled plasma mass spectrometry (ICPMS) and optical emission spectroscopy (OES) are the most powerful techniques for elemental analysis with a variety of applications such as environmental, geological and geochemical, clinical and biomedical, forensic, semiconductor, etc. The success of ICP is due in part to presenting much higher temperatures in comparison with other ionization/excitation sources, longer particle residence time, better control over the chemical environment (as opposed to flames), minimized matrix effects, and less background signal.

Figure 9:
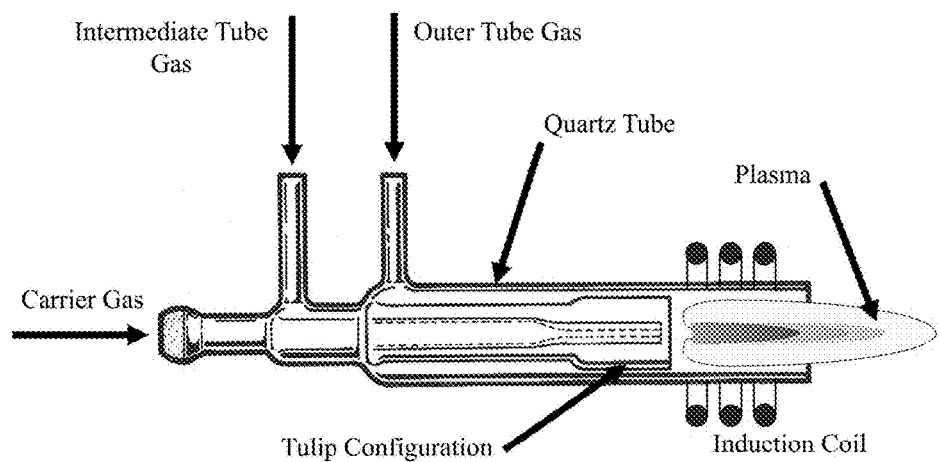
FIG. 9 is an image of an example Fassel torch design.
Figure 10:
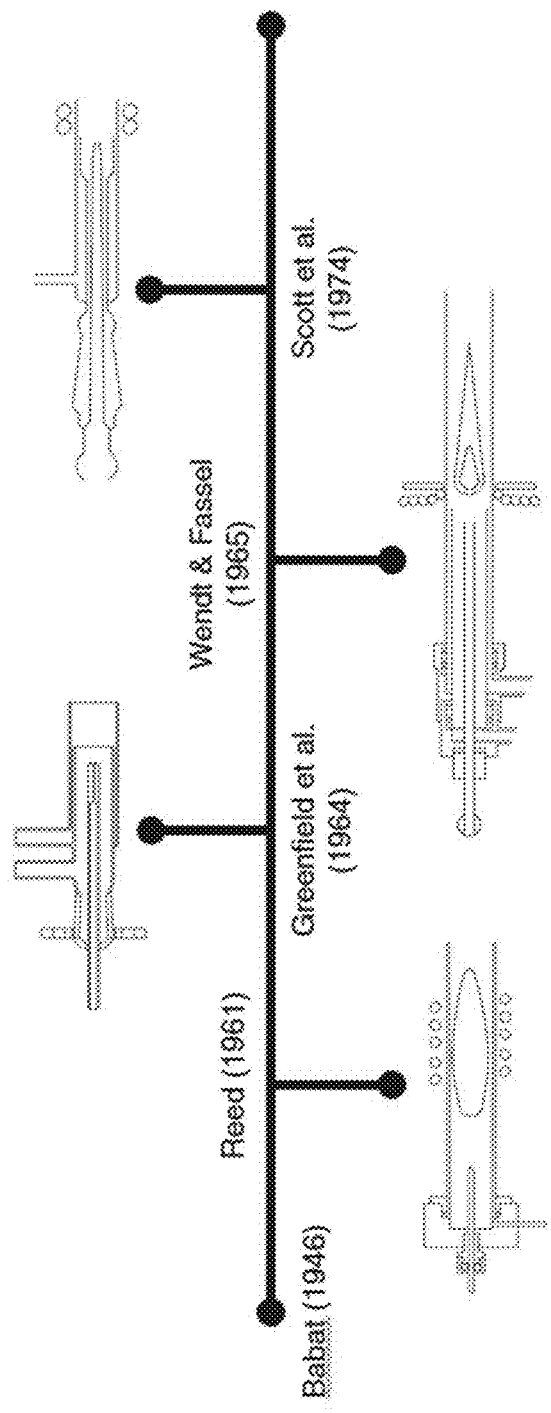
FIG. 10 is a timeline of previous torch designs.

In 1974, Fassel unveiled the final version of a family of ICP torches which has been adopted by most instrument manufacturers since then. The popularity of the Fassel torch over similar torches is due to its lower consumption of argon gas and radio-frequency (RF) power which are both considered favorable economic factors. The same factors later encouraged many researchers to improve the Fassel torch through various optimization procedures, building the torch with materials other than quartz, using alternative gases such as helium or nitrogen, external cooling with air/water, enhancing the swirling flow pattern inside the torch, and size reduction. An example Fassel torch is shown in FIG. 9. A timeline of torch designs is shown in FIG. 10. Of note, the torches shown in FIG. 10 have a cylindrical architecture encapsulating the plasma.

A primary difficulty with reducing argon flow in ICP torches is that the torch may be overheated and/or melted at lower flow rates. Size reduction has been always limited by the electromagnetic skin effect and cannot be used in the current fashion as a remedy to increase the cooling efficiency of the outer gas. Instead, some researchers tried building the torch from other materials (mostly h-BN) instead of quartz. But these materials contaminate the plasma at high temperatures and are not transparent as required for OES. Alternatively, other researchers used water/air to cool the torch wall. Water cooling was very soon rejected due to lowering the sensitivity of plasma and possible disastrous consequences in case of malfunction. Aircooled torches, on the other hand, suffer from plasma contamination due to entrapment of air. Later, some researchers attempted to solve this issue by implementing a cooling jacket around the torch to confine the flow of air. Others tried new torch designs in combination with significantly high amounts of air flow to cool the torch externally. However, many of these torches suffered from loss of sensitivity, high level of oxides, and poor analytical performance.

As such, the Fassel torch still remains a favorable torch for ICP-based spectrometry. Today, a typical ICP-OES/MS instrument may consume around 14-17 L/min of argon and 1200-1600 W RF power to sustain a robust analytical plasma. Since argon is produced by a costly fractional distillation process, it is an expensive gas and contributes to the cost per analysis in ICP-based systems. Also, high consumption of argon is a major hurdle to using these technologies in countries with limited/no resources of argon. From another viewpoint, less RF energy consumption can lead to compact portable instruments with smaller RF generators. In addition, in a world concerned with environmental issues, now more than ever, saving energy, whether directly or indirectly, is of value.

Herein, an ICP torch is disclosed comprising different features than any variation of conventional torches shown in FIG. 10. Design and optimization of the torch was carried out based on four important factors: fluid flow patterns, heat transfer, plasma physics, and analytical performance. Computer simulations were used to design a torch rather than merely studying the already-designed torches. Hundreds of simulations were performed—considering the Navier-Stokes, energy, and Maxwell equations—to obtain a design with optimum flow patterns and maximized heat transfer efficiency. The result is an iconic "conical" torch as opposed to common "cylindrical" ICP torches. Next, Fundamental characteristics of the plasma such as electron number density, and excitation and rotational temperatures were measured experimentally. Furthermore, analytical performance of the torch was investigated by determining plasma robustness, detection limits, and matrix effects. For comparison, these parameters were also determined for a conventional Fassel torch which was mounted on the very same apparatus. As elaborated in the following sections, the result is a conical torch with significant decrease in gas and power consumption but even better analytical performance.

Methods

Instrumentation

Figure 11:
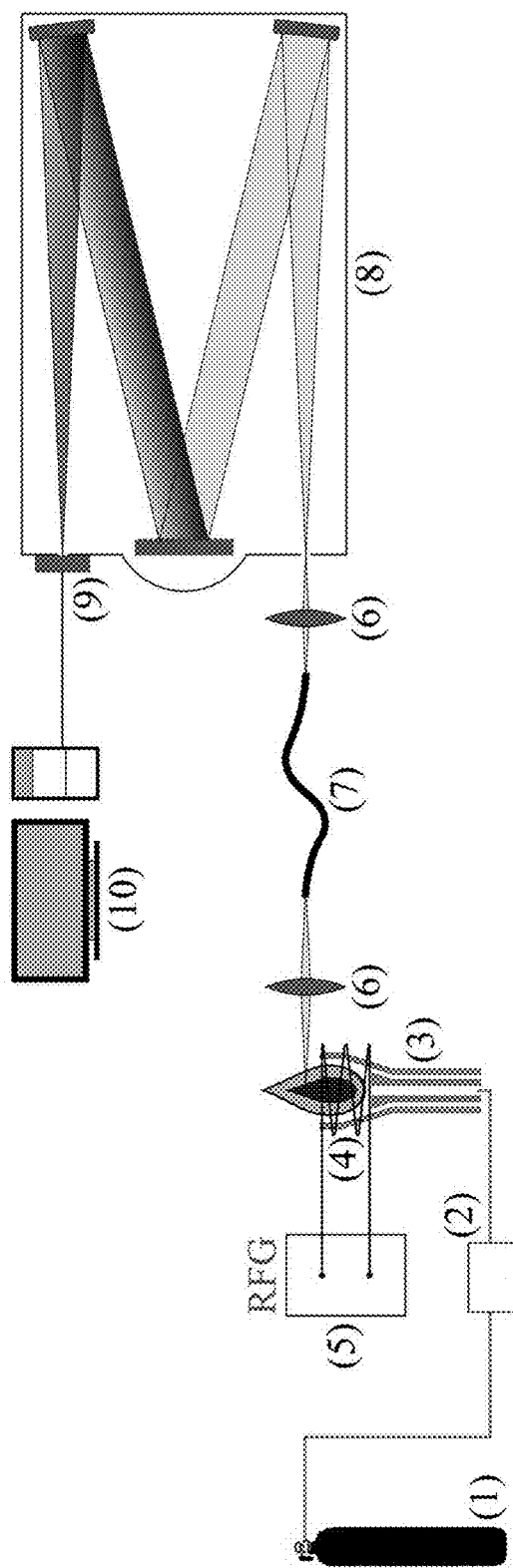
FIG. 11 is a schematic of the experimental setup for testing and characterizing the new torch. (1) Argon supply, (2) mass flow controller, (3) ICP torch, (4) load coil, (5) RF generator, (6) quartz lenses, (7) UV-VIS optical fiber, (8) monochromator, (9) CCD, (10) computer for data collection.

To test the new torch, an experimental setup was prepared as schematically shown in FIG. 11. A free-running RF generator (nominal 40 MHz, Colpitts-type, PerkinElmer/SCIEX, Canada) was used to provide the power to a balanced load coil for sustaining the plasma. Values of the plate voltage and current of the RF oscillator were used to estimate the plasma power. To characterize the plasma, a monochromator (Triax550, HJY, USA) was used in combination with a charge-coupled detector (CCD) (CCD3000, Spectrum-One, HJY, USA). The CCD was always cooled with liquid nitrogen to minimize the dark current noise. The photons emitted from the plasma were focused to the aperture of a flexible UV-VIS optical fiber. A set of motorized linear stages were used to move the fiber and scan the plasma at any desired point with a spot size of approximately 0.7 $mm^2$. Another lens set was used to collect the light from the fiber and focus it to the entrance slit of the monochromator. The diffraction grating used in the monochromator had a 1200 grooves/mm density. For all the tests, 11 consecutive integrations of the desired spectral line were acquired. The integration times were adjusted based on the sensitivity of the target lines.

For sample introduction to the plasma, a typical pneumatic concentric nebulizer (Type-A, Meinhard, USA) was used in combination with a baffled cyclonic spray chamber (PerkinElmer Inc., USA). A peristaltic pump (Ismatec REGLO ICC digital 2-channel pump, Cole-Parmer, USA) was used to keep the sample uptake rate fixed at 1 mL/min for all the experiments. Details of the reagents used for all the analyses are described in the Supporting Information.

Computer Simulations

A 2D-axisymmetric numerical model was developed based on Mostaghimi and Boulos to study the steadystate ideal-gas Newtonian fluid flow and heat transfer inside the new torch. In this model, the ANSYS-FLUENT software was used to solve the Navier-Stokes, energy, species transport, and Maxwell equations simultaneously. In addition to the axial and radial equations, the axisymmetric tangential momentum equation was also included to account for the effects of swirl velocity inside the torch. It may be noted that in an axisymmetric situation, all the derivatives in the azimuthal (tangential) direction are identically zero. The Maxwell equations were added to the software in the form of user-defined functions (UDF) and scalars (UDS) to account for the electromagnetic effects (i.e. Joule heating and Lorentz forces). The ICP was assumed to be in a local thermal equilibrium (LTE) condition and optically thin. To treat the electromagnetic boundary conditions, the extended field approach was used. To account for the effects of the surrounding air on the ICP, the species transport model was solved as well. In addition, the discrete phase model (including evaporation and breakup) was included to simulate the interaction of sample aerosol with the ICP.

Results and Discussion

Torch Design Methodology

Figure 12A:
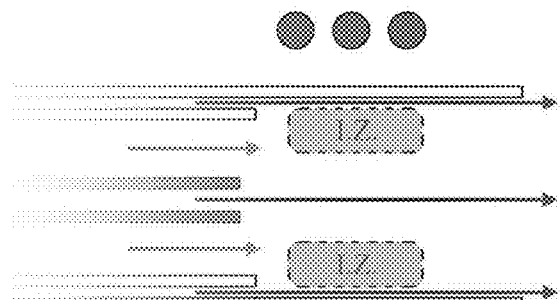
FIG. 12A shows Schematics of a conventional 3-tube Fassel torch.
Figure 12B:
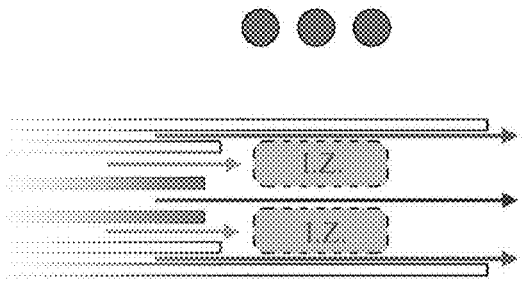
FIG. 12B shows the smallest version of a Fassel/cylindrical torch before the sample stream interferes with the energy induction zone (I.Z.).

To design a new ICP torch, several factors should be taken into account. One limiting factor is the electromagnetic skin depth which is estimate to be around 2 mm for argon ICP at an average temperature of 8000K. Therefore, the minimum torch diameter would be around 12 mm (as depicted in FIG. 12B) if we want to obtain an annular plasma for which the sample stream does not interfere with the induction zone. In fact, smaller torches have been built, tested and proven to be inferior to the Fassel torch due to interferences from easily-ionizable elements (EIE).

Another important objective in designing a new torch is to increase the cooling efficiency of the outer gas as much as possible to prevent the torch from thermal damage at lower flow rates. Based on heat transfer fundamentals, this is possible by increasing the speed of outer gas which leads to an increase in the Reynolds number. This would result in the Nusselt number and hence the convective heat transfer coefficient on the outer tube to be increased. However, with a torch diameter of 12 mm, only 50% increase in gas velocity is achievable in comparison with the Fassel torch. Therefore, another design strategy has been followed.

Figure 12C:
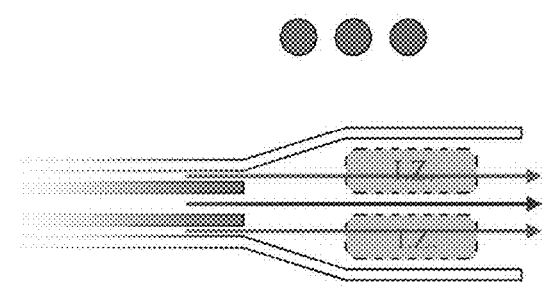
FIG. 12C shows a 2-tube conical torch with significant increase in gas velocity.

To achieve a significant increase in outer gas velocity, as shown in FIG. 12C, instead of decreasing the torch diameter altogether, in this work the diameter of the portion upstream the plasma has been reduced. This would give the new torch a "conical" shape in contrast to conventional torches which are "cylindrical". The intermediate tube has also been removed to provide more space for size reduction. With this modification, 150% increase in gas velocity can be achieved.

Figure 12D:
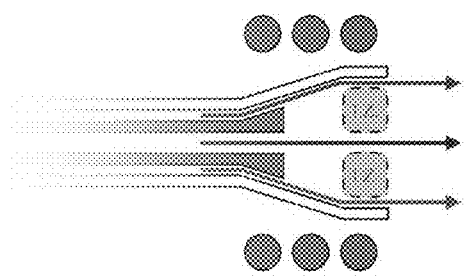
FIG. 12D shows Schematics of the new torch concept with modified injector tube to prevent the outer gas from extinguishing the plasma.

In addition, the tip of the injector tube should be modified in concert with the outer tube to prevent the outer gas from going straight into the energy induction zone and extinguishing the plasma. In addition, the smaller size of the torch leads to higher power density in the plasma which can be used to reduce energy consumption. Such a design concept is shown in FIG. 12D for which all the geometrical dimensions should be optimized.

Optimization of Geometrical Parameters

FIGS. 13A and 13B show the geometrical parameters of an embodiment of the new torch and those of an example Fassel torch. For the Fassel torch, these parameters have been optimized throughout the years. Here, a thorough optimization has been carried out on several parameters of the new torch.

Based on the simulations, the optimum gap g between the outer and injector tubes was found to be 1 mm. A larger gap decreased the outer gas velocity and its cooling efficiency. Conversely, a smaller gap formed a layer of outer gas which was too thin and not able to minimize heat conduction from the plasma to the outer tube.

Another important geometrical parameter of the new torch is the aspect ratio h/w which defines the slope of increasing the torch radius from r3 to r4. Based on the simulations, increasing this ratio causes the total gauge pressure to become largely negative on the central axis of the torch. As a result, the plasma would be effectively pulled towards the injector tube which, in turn, leads to a very stable plasma. This behavior is peculiar to the new torch, mostly due to its conical geometry as opposed to common cylindrical torches. In contrast to the Fassel torch which is said to be sensitive to ingression of air or sudden changes in sample stream, the new plasma was seen to be considerably more resistant to these effects. Nevertheless, excessive increase of the aspect ratio would place the plasma too close to the injector tube which might lead to some thermal damage. To find the optimum value of this ratio using simulations, it was varied while several parameters such as temperature and position of the plasma, maximum temperature on the injector and outer tubes, flow pattern of various gases, velocity of the outer gas, etc., were carefully inspected. A value of 0.32 was found to provide the maximum plasma temperature while satisfying the criteria mentioned above.

The outer radius of the injector tube was fixed at 2 mm. This would give the inner radius r1 enough range (up to 1.5 mm) to choose from depending on the application. Consequently, the minimum inner radius at the neck of the torch r3 is forced to be 3 mm. In addition, the tip of the injector tube was set to have a radius r2 slightly greater than r3 to prevent the gas from going into the induction zone and direct the gas towards the outer tube.

Table 1 summarizes all the geometrical parameters of the new torch along with those of a conventional Fassel torch (associated with FIGS. 13A and 13B). Based on these dimensions, the torch cavity (i.e., the region in which the plasma is formed) would be about 6.7 times smaller for the new torch compared to that of the Fassel torch. This translates into a significantly higher power density for the new torch. The ratio of dimensions h to w shown in FIG. 13A are equivalent to the conical ratio b/a described earlier.

FIGS. 14A and 14B show the constructed version of the new torch (by Precision Electronic Glass Inc., Vineland, USA) with these dimensions. The outer gas inlet tube was connected tangentially to form a swirling flow inside the torch. The injector and outer tubes were mounted on a polycarbonate torch holder in a concentric manner.

FIGS. 15A and 15B show the simulated distribution of temperature and streamlines in the new and Fassel torches. To mimic the real-time operation of the torch, 20 μL/min of water aerosol (with a uniform 5 μm drop-size distribution at the injector inlet) was introduced to the plasma. The simulations could predict the droplet trajectories, size change, and vaporization of these particles due to interaction with plasma.

As a result of size reduction, it is evident that the induction zone inside the new torch is closer to the sample aerosol compared with the Fassel torch. More importantly, the volume of this zone for the new torch (~330 mm$^2$) is almost 4 times smaller than the one for the Fassel torch (~1230 mm$^2$), meaning the power would be dissipated in a much smaller area. Based on simulations, these two effects lead to a 1000K hotter plasma for the new torch. This is while the new torch works with less power and 60% decrease in gas flow rate for the cases shown in FIG. 15A. Due to the conical design, 10 m/s velocity is achieved for 7 L/min gas flow rate. While for the Fassel torch this velocity is close to 6 m/s even at a high flow rate of 15 L/min.

Torch Operation

To test the new torch, it was mounted on the RF generator with a smaller load coil as indicated in Table 1. A 33 pF ceramic capacitor was added in parallel with the smaller load coil to compensate for the decrease in impedance and keep the RF generator resonance frequency unchanged. The plasma could be consistently ignited without any is-sues by introducing 10 L/min of argon as the outer gas, 0.5 L/min for the carrier gas, and generating an electron stream with a piezoelectric igniter. After ignition, the flow could be reduced to the desired value (4-10 L/min) which is based on the selected RF power (300-1500 W). The new torch has been operated in this way for hundreds of hours without any issues or sign of overheating.

TABLE 1

| | New Torch | | Fassel Torch |
|---|---|---|---|
| h (mm) | 1.23 | $L_1$ (mm) | 1.5 |
| g (mm) | 1 | $L_2$ (mm) | 25.5 |
| $l_1$ (mm) | 13.4 | $L_c$ (mm) | 5 |
| $l_2$ (mm) | 4 | $P_c$ (mm) | 5 |
| $l_c$ (mm) | 2.6 | $R_1$ (mm) | 0.5-1 |
| $p_c$ (mm) | 4.4 | $R_2$ (mm) | 2 |
| $r_1$ (mm) | 0.5-1 | $R_3$ (mm) | 7 |
| $r_2$ (mm) | 3.23 | $R_4$ (mm) | 8 |
| $r_3$ (mm) | 3 | $R_5$ (mm) | 9 |
| $r_4$ (mm) | 6 | $R_c$ (mm) | 15 |
| $r_e$ (mm) | 10 | $R_f$ (mm) | 1.625 |
| $r_f$ (mm) | 1.625 | $T_w$ (mm) | 1 |
| $t_w$ (mm) | 1 | | |
| w (mm) | 3.87 | | |
| Outer gas (L/min) | 4-10 | Outer gas (L/min) | 12-15 |
| Intermediate gas (L/min) | — | Intermediate gas (L/min) | 0.2-1.2 |
| Outer tube material | quartz | Outer tube material | quartz |
| Injector tube material | quartz | Injector tube material | quartz |

Characteristics of the Plasma

Electron number density, excitation temperature, and rotational temperature are among the most important fundamental properties of ICP which directly affect ionization/excitation of sample and analytical performance. To measure these properties for the new torch, outer gas and power were set to 7 L/min and 900 W, respectively. Three different injectors with inner radii of 0.5 mm, 0.7 mm, and 1.0 mm were tested to investigate the effect of injector size on these properties. For these injectors, carrier gas was set to 0.5, 0.7, and 0.9 L/min, respectively. For the Fassel torch, outer gas, carrier gas, and power were set to 15 L/min, 1 L/min, and 1100 W, respectively. A typical injector with inner radius of 1.0 mm was used for this torch. For all the measurements, both torches were operated horizontally with the plasma observed in radial (side-on) mode.

Excitation Temperature

For both torches, excitation temperatures were determined at various observation heights using the Boltzmann plot with seven Fe atomic lines. Properties of the emission lines were obtained from the NIST database. Values of r-squared for the Boltzmann plots were in the range of 0.966-0.998.

FIGS. 16A and 16B show the variation of excitation temperature against observation height for both torches. On average, for the new torch, the excitation temperature is about 1600K higher than that of the Fassel torch. As previously discussed for FIGS. 15A and 15B, this significant improvement is certainly due to the higher power density inside the new torch and proximity of the sample stream to the induction zone. Furthermore, for the injector tube with inner radius of 0.5 mm, excitation temperature is higher than the other injectors.

FIGS. 17A and 17B show the simulated temperatures on the central axis of both torches. These values are about 1000K higher compared with Fe excitation temperatures measured experimentally. This can be attributed to less accuracy of LTE assumption for simulations at the center of plasma. Also, for experiments, excitation temperature was measured using Fe lines, while this could not be done in the simulations. Nevertheless, simulations show a similar trend and that the new torch presents 1000K higher temperature compared with the Fassel torch. Like the experiments, the 0.5 mm injector provides the highest temperature among others.

Rotational Temperature

To determine the rotational temperatures based on the Boltzmann plot, nine Q1 lines of the OH ($A^2\Sigma^+ \rightarrow {}^2\Pi$) band were observed. During these measurements, deionized water was continuously injected into the plasma. R-squared values for the Boltzmann plots were all in the range of 0.860-0.939.

The results are shown in FIGS. 18A and 18B. For the new torch rotational temperatures are about 1200K more than those of the Fassel torch due to the reasons mentioned previously. Again, for the injector with inner radius of 0.5 mm, temperatures are higher.

FIG. 19A shows variation of electron number density against observation height after the load coil for the new torch. FIG. 19B shows variation of electron number density against observation height after the load coil for the Fassel torch.

Electron Number Density

Finally, based on the Stark broadening of the Hβ (486.1333 nm) Balmer emission line, values of electron number density ne were determined. De-tails of the relations used to calculate electron number density are described in the Supporting Information. Spectroscopic properties of the Hβ line were taken from the NIST line database. For these measurements, deionized water was continuously injected into the plasma. For the new torch electron number density is between 4 to 5 times higher than the Fassel torch. Similarly, the 0.5 mm injector exhibits the highest electron number densities. This leads to higher plasma robustness, less matrix effects, and better multi-element analysis capability as shown in the following sections.

Analytical Parameters

FIGS. 20A, 20B, 20C and 20D show the images of both torches with different operating conditions captured by a Nikon D90 camera with a 105 mm AF MICRO NIKKOR lens. The images on the left and right columns show the plasma without and with injecting yttrium solution, respectively. The initial radiation zone (IRZ), and normal analytical zone (NAZ), and recombination zone (RCZ), each of which characterized by a different emission color, are shown with arrows. All the images have the same exposure/shutter-speed for comparability.

As expected, due to the physical parameters of the plasma, at same power of 1000 W, the new torch generates a much brighter plasma than the Fassel torch. Even at 800 W, the plasma is brighter in the new torch compared to the one formed in the Fassel torch. This is while the new torch is operated at ½ to ⅓ the outer gas flow of the Fassel torch.

Moreover, injection yttrium solution into both plasmas (FIGS. 20A, 20B, 20C and 20D) shows that the new torch is capable of both ionizing and exciting the sample particles even at lower plasma powers. Furthermore, the normal analytical zone (NAZ), characterized by a blue color for excited Y+, is slightly brighter for the new torch in comparison with the Fassel torch. In addition to having a higher excitation temperature as shown before, this is a sign that the excited species are concentrated in a smaller region. Also it can be seen that the optimum observation height for the new torch is shorter than that for the Fassel torch.

Plasma Robustness

It has been proposed that the intensity ratio of Mg II 280.2704 nm/Mg I 285.2127 nm lines is a measure of plasma robustness in optical spectrometry. In order to account for different diffraction efficiency of the spectrometer at various positions, it has been suggested a correction factor be used based on the ratio of background emissions BG285/BG280 close to the target Mg lines. We obtained an average value of 1.3 for our spectrometer.

FIGS. 21A and 21B show the values of Mg II/Mg I for both torches at various observation heights. The values of robustness for the Fassel torch are around 4.3 which is in agreement with conventional results. Nevertheless, the new plasma is almost 3 times more robust than the one generated by the Fassel torch. This superiority can be explained based on the Saha and Boltzmann equations which relates ionic/atomic line intensity ratio to electron number density and temperature. Therefore, a 5-time increase in electron number density leads to about 3 times the robustness for the new torch. Also, it is stated that higher ionic/atomic line intensity ratios represent a closer condition to LTE.

Detection Limits

To determine the detection limits for both torches, single-element solutions of the metallic elements were injected into the plasma. All the solutions were prepared in 2% HNO3 in deionized water with the concentrations suggested in conventional literature. Detection limits cL were calculated based on the 3σ criterion. A background correction method was applied to determine the background signal and its relative standard deviation RSDBG, based on conventional methods for CCDs. A line-free region of the background emission was chosen and a straight line was fitted to the background points. Then the sum-of-squared-residuals SSR between the fitted line and background points were used to calculate the RSDBG as follows (equation 1):

$$RSDBG = \frac{\sqrt{SSR}}{BG \times (n-1)}$$

where BG is the background signal determined by the fitted line, and n is the number of background points.

To find the best operational parameters for measuring detection limits, it had been suggested to use robustness as a criterion. However, it is clear that increasing power leads to higher Mg II/Mg I ratios. Therefore, robustness will not provide any information regarding the optimum power. In addition, this criterion is usually seen to suggest lower carrier gas at shorter observation heights which are far from the actual optima for these parameters. As seen in FIGS. 22A and 22B, the maximum signal-to-background ratio (SBR) for the Mg II line lies at 7.5 mm and 15.5 mm heights for the new and Fassel torches, respectively. This is while maximum robustness is obtained at shorter heights of 6.5 mm and 10.5 mm as seen in FIGS. 21A and 21B. At these observation heights, SBRs are considerably lower than the maximum values.

Furthermore, spectral lines behave differently against variation of operational parameters depending on being hard or soft. Therefore, it has been suggested to change the power, carrier gas, and observation height one by one for each spectral line to obtain the highest SBR. Here we followed a similar approach. For observation height, the values obtained from FIGS. 22A and 22B were chosen as optimum for both torches. For the new torch, three power levels (i.e., 500 W, 700 W, and 900 W) were considered. For each power, and depending on the injector size, the carrier gas was gradually increased from low to high values with a step-size of 0.05 L/min. For the Fassel torch, carrier gas and power were set to 1 L/min and 1100 W, respectively. Table 2 summarizes the detection limits, SBRs, and background equivalent concentrations (BEC) for the most prominent line of each element. These elemental lines were chosen based in part on capabilities of our spectrometer and freedom of overlap with OH bands whenever possible. The detection limits obtained for the Fassel torch in this work are generally improved in comparison with the conventional reported values. Also, for most of the elements, detection limits, SBRs, and BECs for the new and Fassel torches are in the same order of magnitude; although for a few lines SBRs are considerably higher for the new torch. Nevertheless, it can be safely concluded that the performance of both torches in single-element analysis is comparable. This is while the new torch was operated with 50% less gas and power consumption.

FIGS. 23A and 23B show example optimum values of power and carrier gas scattered against energy sum (i.e., sum of ionization energy and/or excitation energy of the upper level of the line) for the 0.5 mm injector. A clear correlation between power and energy sum can be seen. The spectral lines can be divided into three categories with respect to power. The lines with the energy sum less than 5 eV are all atomic for which 500 W power is optimal (except for Ag I). For these lines, which can be considered "soft", we observed that increasing power deteriorates SBR. A portion of the ionic lines, having 8 eV to 10 eV energy sum, need an intermediate power of 700 W. Upon increasing the power to 900 W, a small decrease in detection limits was observed. For the rest of the ionic lines with high energy sum the optimum power was 900 W.

For carrier gas, no clear trend can be distinguished and the optimum values are scattered around an average value of 0.54 L/min. The exception is Na I for which the best SBR ratio could be obtained at unusually high carrier gas flow rates. This behavior was observed for all injector sizes.

Matrix Effects

To test the effects of EIEs on elemental analysis for both torches, 2% HNO3 solutions containing 1 μg/mL Mg and seven different concentrations of Na (0.03% to 4%) were consecutively injected into the plasma. Between each injection, the blank solution was injected for several minutes to wash the sample introduction path. FIGS. 24A and 24B show the decrease and increase in Mg II and Mg I line intensities, respectively. Primarily, the decrease in the Mg II line intensity for the new torch with the smallest injector tube is at most 5%. In contrast, Mg II line for the Fassel torch experiences a 33% fall in intensity. In addition, as the size of the injector inner radius for the new torch is increased from 0.5 mm to 1.0 mm, the effect of Na interference be-comes more effective; although it remains well below the value obtained for the Fassel torch.

This experiment confirms that a robust plasma with a high level of electron number density, as in the new torch, is indeed less prone to matrix effects. In addition, the values of net signal intensity of both the atomic and ionic Mg lines are significantly higher for the new torch which translates into higher sensitivity of the plasma.

Multi-Element Analysis

Table 2 summarizes the analytical performance of both torches as discussed in the preceding sections. Based on all these results, it seems that the optimum injector size for the new torch is the one with 0.5 mm inner radius. Detection limits for all the injectors are in the same order. But the 0.5 mm injector presents the highest excitation/rotational temperatures, electron number density and robustness with minimum EIE interference.

Table 2 shows detection limits, SBRs, and BECs for the new and Fassel torches obtained at their optimized operating conditions and using single-element solutions. The spectral lines are sorted based on their energy sum; i.e., sum of ionization (if applicable) and excitation energies.

TABLE 2

| | | | | | | | | | | | | | Fassel | | |
|---|---|---|---|---|---|---|---|---|---|---|---|---|---|---|---|
| | | | | | | | | | | | | | | $C_L$ (ng/mL) | |
| | | | | New torch Injector inner radius (mm) | | | | | | | | | | conventional | |
| | | $C_0$ | 0.5 | | | 0.7 | | | 1.0 | | | | | liter- | |
| Line | λ (mm) | (μg/mL) | SBR | BEC (ng/mL) | $C_L$ (ng/mL) | SBR | BEC (ng/mL) | $C_L$ (ng/mL) | SBR | BEC (ng/mL) | $C_L$ (ng/mL) | SBR | BEC (ng/mL) | this work | ature results |
| Na (I) | 588.995 | 10 | 794 | 12.6 | 1.3 | 592 | 16.9 | 1.3 | 425 | 23.5 | 1.8 | 61.4 | 163 | 1.6 | 29 |
| Ag (I) | 328.068 | 10 | 15.4 | 649 | 13 | 9.34 | 1070 | 10 | 10.1 | 990 | 11 | 22.8 | 439 | 8.0 | 7 |
| Al (I) | 396.152 | 10 | 189 | 52.9 | 1.7 | 126 | 79.4 | 1.7 | 98.4 | 102 | 2.3 | 10.4 | 961 | 6.5 | 28 |
| Bi (I) | 306.772 | 100 | 54.0 | 1850 | 34 | 61.8 | 1620 | 32 | 43.8 | 2280 | 34 | 29.5 | 3390 | 29 | 75 |
| Au (I) | 267.595 | 100 | 56.8 | 1760 | 23 | 45.9 | 2180 | 19 | 39.8 | 2510 | 18 | 38.0 | 2630 | 11 | 31 |
| Ge (I) | 265.118 | 100 | 20.1 | 4980 | 69 | 16.0 | 6250 | 51 | 11.7 | 8550 | 50 | 17.0 | 5880 | 22 | 48 |
| Ba (II) | 455.403 | 1 | 126 | 7.94 | 0.12 | 102 | 9.80 | 0.12 | 47.2 | 21.2 | 0.15 | 91.4 | 10.9 | 0.12 | 1.3 |
| Sr (II) | 407.771 | 1 | 198 | 5.05 | 0.056 | 176 | 5.68 | 0.058 | 142 | 7.04 | 0.069 | 209 | 4.78 | 0.054 | 0.42 |
| Ca (II) | 393.366 | 1 | 371 | 2.70 | 0.034 | 236 | 4.24 | 0.037 | 251 | 3.98 | 0.042 | 161 | 6.21 | 0.067 | 0.19 |
| Y (II) | 371.029 | 10 | 199 | 50.3 | 1.5 | 176 | 56.8 | 1.7 | 113 | 88.5 | 1.4 | 94.4 | 106 | 1.8 | 3.5 |
| Lu (II) | 261.542 | 10 | 36.8 | 272 | 4.5 | 14.0 | 714 | 3.8 | 25.4 | 394 | 3.6 | 42.0 | 238 | 1.3 | 1.0 |
| Mg (II) | 279.553 | 1 | 23.0 | 43.5 | 0.25 | 32.7 | 30.6 | 0.18 | 38.5 | 26.0 | 0.15 | 60.5 | 16.5 | 0.19 | 0.15 |
| Mn (II) | 257.610 | 10 | 20.4 | 490 | 1.9 | 17.9 | 559 | 1.8 | 14.3 | 699 | 1.5 | 23.6 | 424 | 2.1 | 1.4 |
| Fe (II) | 259.949 | 10 | 3.50 | 2860 | 16 | 4.03 | 2480 | 12 | 4.41 | 2270 | 9.3 | 7.15 | 1400 | 5.4 | 6.2 |
| Be (II) | 313.042 | 1 | 60.4 | 16.6 | 0.073 | 65.6 | 15.2 | 0.089 | 34.8 | 28.7 | 0.078 | 82.3 | 12.2 | 0.15 | 0.27 |

Table 3 shows values of analytical/physical parameters for the new and Fassel torches measured at the optimized observation height and carrier gas.

TABLE 3

| Parameter | New Torch | | | Fassel Torch |
|---|---|---|---|---|
| Injector inner radius (mm) | 1.0 | 1.4 | 2.0 | 2.0 |
| Observation height (mm) | 7.5 | 7.5 | 7.5 | 15.5 |
| Carrier gas (L/min) | 0.5 | 0.7 | 0.9 | 1 |
| Power (W) | 900 | 900 | 900 | 1100 |
| Outer gas (L/min) | 7 | 7 | 7 | 15 |
| Intermediate gas (L/min) | — | — | — | 0.2 |
| Excitation temperature (K) | 6980 ± 383 | 6970 ± 286 | 6780 ± 242 | 5314 ± 262 |
| Rotational temperature (K) | 4960 ± 470 | 4524 ± 332 | 4656 ± 404 | 4022 ± 339 |
| Electron No. density (×10$^{15}$ (1/cm$^3$)) | 4.39 | 2.94 | 2.75 | 0.82 |
| Robustness (Mg II 280/Mg I 285) | 12.3 | 10.7 | 10.4 | 4.3 |
| EIE interference (% decrease in Mg II signal due to 4% Na) | 5.5% | 11.3% | 18.6% | 33.4% |

Modeling Effect of Conical Ratio on Performance

As described below and seen in FIGS. 26A, 26B, 26C, 26D, 27, 28A, 28B, and 28C, a range of conical shapes and aspect ratios provide benefits including higher plasma temperature, improved protection of the torch body from the plasma, and stability of the plasma.

As shown in the simulation FIGS. 26A, 26B, 26C, 26D, a smaller conical ratio may cause the plasma to stand farther from the injector. This behavior is due to the shear forces exerted on the plasma by the outer gas. As the conical ratio is decreased, the axial component of these forces is enhanced and the plasma is further pushed out of the torch. Eventually, if the ratio is decreased too much, the plasma would be pushed out of the torch and extinguished. Also, based on values of magnetic flux density, decreasing the aspect ratio may intensify the magnetic field inside the torch. On the other hand, increasing the aspect ratio seems to have a stabilizing effect on the plasma. This can be explained by the effect of the outer gas on pressure distribution inside the torch.

FIG. 27 shows the computer-simulated variation of the total gauge pressure along the torch radius (normalized with r4 for the new torch and R5 for the Fassel torch described in FIGS. 13A and 13B) for various outer gas flow rates. Carrier gas flow rate is set to 1 L/min for all the cases. The h/w ratio for the new torch modeled in FIG. 27 is 0.318. The power is set to zero and plasma is extinguished to investigate the pressure variations independently from the effects of plasma.

FIG. 27 shows the variation of total gauge pressure (i.e., sum of the dynamic and static gauge pressures) along the radius of both the new and Fassel torches for various outer gas flow rates. It is clear that for the new torch at 8 L/min, the total gauge pressure at the center of the torch is much lower than the peripheral regions. This advantageous behavior is exclusively exhibited by the new torch due its conical design. Although, the presence of plasma may affect the whole flow pattern and pressure distribution, the combined effect of torch design and outer gas velocity, as described here, would still make its own contribution to the pressure fields inside the plasma.

To better understand the underlying cause of this behavior, FIGS. 28A, 28B and 28C show the velocity vectors inside the new and Fassel torches. Carrier gas flow rate for all the cases is set to 1 L/min and the intermediate gas (only for the Fassel torch) is set to 1.2 L/min. The h/w ratio for the new torch is in this example 0.318. The power is set to zero and plasma is extinguished.

It can be seen that the gas velocity for the new torch at 8 L/min (FIG. 28A) is significantly higher than that for the Fassel torch at the same (FIG. 28B) and even 15 L/min (FIG. 28C) flow rate. This improvement in velocity of the outer gas, in combination with the gradual increase in torch diameter, forms a circulation zone (as observed based on velocity vectors) inside the new torch which causes the plasma to be effectively pulled in. On the contrary, for a "cylindrical" torch such as Fassel's the effect is very weak and can hardly contribute to plasma stabilization, especially at lower flow rates (FIG. 27).

Based on the above discussion, the influence of the aspect ratio h/w on plasma stability can be explained by looking at two competing phenomena: one is the effect of shear forces exerted by the outer gas on the plasma; the other is the amount of negative pressure the outer gas can generate inside the central regions of the torch with respect to its periphery. Generally, the former works to push the plasma out of the torch while the latter tries to prevent that from happening.

In contrast, the conical torch has the dual benefit of increasing the velocity of the outer gas for torch cooling and generating stronger fields of negative pressure inside the torch for stabilization. Also, FIGS. 26A, 26B, 26C and 26D demonstrate that increasing the h/w ratio enhances this effect and pulls in the plasma with greater force. Therefore, for h/w=0.578 the plasma is closer to the injector tube compared to the other cases. However, it should be taken in mind that the aspect ratio should not be overly increased otherwise the injector tube will be overheated. On the other hand, decreasing the aspect ratio leads to a higher plasma temperature due to the smaller size of the torch and higher energy density.

Comparison of New and Fassel Torches as a Function of Flow Rate

FIGS. 29A, 29B, 29C, 29D, 29E and 29F show the results of simulations for both torches at various flow rates. The power, intermediate gas (only for the Fassel torch), and carrier gas flow rates are set to 1000 W, 1.2 L/min, and 1 L/min, respectively. The power induction zone (I.Z.) inside the plasma is determined based on 1/e maximum current density. Interestingly it can be seen that the energy induction zone for the new torch is smaller compared to the Fassel torch. This leads to at least 4 times power density inside the new torch. As a result, with the same power and flow rate, the plasma inside the new torch (FIG. 29D) is about 1000 K higher compared to the Fassel torch (FIG. 29E). On the other hand, simulations showed that, for 8 L/min, the average velocity of the outer gas in the new torch is ~10 m/s as compared to a ~3 m/s for the Fassel torch at the same flow rate (FIG. 29A). In other words, the conical design has led to more than 3-fold improvement in the cooling efficiency of the outer gas. Therefore, even for a flow rate as low as 6

L/min (FIG. 29B) the maximum temperature on the outer tube was obtained to be around 540 K which is well below the allowable working temperatures of quartz6. At such a low flow rate, the plasma would be very unstable inside the Fassel torch as proved by simulations and experiments.

FIG. 30A shows variation of outer gas velocity at the point of discharge between the outer tube and injector/intermediate tube for the new/Fassel torches. FIG. 30B shows variation of temperature along the central axis of the new and Fassel torches. The power, intermediate gas (only for the Fassel torch), and carrier gas are set to 1000 W, 1.2 L/min, and 1 L/min, respectively. The extent of both torches are shown in (b) for better comparison.

FIG. 30B indicate this temperature is 1000 K higher for the new torch at the same power. Aside from the effect of power density, the smaller size of the new torch may cause the energy induction zone to be closer to the sample stream as seen in FIGS. 29A, 29B, 29C, 29D, 29E and 29F.

Experimental Conclusion

A new ICP torch was designed, constructed, and tested based on a new methodology. Initially, computer simulations, capable of accounting for the magneto-hydrodynamic effects, were used to design the torch and optimize its geometrical parameters for the first time. Based on plasma physics, fluid flow patterns, and heat transfer, simulations resulted in the concept of a conical torch as op-posed to common cylindrical ones. As described in the experimental section herein, the conical geometry made it possible to increase the gas velocity by 150% resulting in 50-70% less argon consumption. Additionally the power density in the new torch is more than 4 times the power density of conventional torches. This is the result of size reduction. Based on the experimental results, these advantages led to significantly higher excitation/rotational temperature and electron number density. Measurements of Mg II/Mg I line intensity ratios showed that the new plasma is highly robust, even at lower powers, causing it to be less prone to matrix effects. Detection limits were determined and compared in single (summarized in Table 2) and multi-element (shown in FIG. 25) analyses which demonstrated the superior capabilities of the new conical torch. In summary, compared to the Fassel torch, the new torch consumes up to 70% less argon and 50% less power and has better analytical performance.

The torch of the subject invention may be integrated in an elemental analyzer system and workflow.

For example, as shown in FIG. 31, a torch of the subject invention may be integrated in a mass spectrometry system and workflow. Sample may be introduced though a nebulizer and/or spray chamber, and carried through an injector inlet of the torch. A gas supply may supply the outer gas flow of the torch. Sample ionized and atomized in the plasma may pass through one or more cones (e.g., one or more sampler cone and skimmer cone) into ion optics, which may include elements such as one or more deflectors, ion lenses, and mass filters. Ions from the sample then pass into the mass analyzer, which may include a mass separation devise and one or more ion detectors. Exemplary mass analyzers include time-of-flight (TOF), magnetic sector, quadrupole, ion traps, and Fourier transform ion cyclotron resonance analyzers.

In another example, the ICP torch of the subject invention may be integrated in a optical emission spectrometry system and workflow, such as shown in FIG. 11.

Alternatively, the ICP torch of the subject invention may be integrated in an atomic absorption spectrometry system and workflow, As used below, any references to a series of examples is to be understood as a reference to each of those examples disjunctively (e.g., "Examples 1-4" is to be understood as "Examples 1, 2, 3, or 4").

What is claimed is:

1. A torch for inductively coupled plasma, the torch comprising:
   a torch tube having a support end and a conical end, wherein a portion of the conical end defines a cavity for confining the inductively coupled plasma;
   an injector tube positioned within the torch tube, wherein the injector tube includes an injector inlet end for receiving a sample flow and an injector conical end; and
   an annular channel defined between an outer wall of the injector tube and an inner wall of the torch tube, wherein the torch tube further comprises a gas inlet for receiving a gas flow.

2. The torch of claim 1, wherein the gas inlet is configured to direct the gas flow into the annular channel with an angular velocity.

3. The torch of claim 2, wherein the torch tube further comprises an elongated neck between the gas inlet and the conical end, wherein the elongated neck defines an angular accelerator that increases the angular velocity of the gas flow.

4. The torch of claim 3, wherein the angular accelerator tapers from a wider diameter to a narrower diameter at the elongated neck.

5. The torch of claim 1, wherein the injector tube is positioned concentrically within the torch tube along a central axis of the torch tube.

6. The torch of claim 1, wherein the outer wall of the injector tube at the injector conical end comprises an injector conical geometry defined by an increase in outer diameter in a downstream direction away from the injector inlet end, and wherein the conical geometry has an injector conical ratio.

7. The torch of claim 6, wherein the conical ratio is in the range of about 0.1 to about 1.5.

8. The torch of claim 7, wherein the conical ratio is in the range of about 0.3 to about 0.6.

9. The torch of claim 8, wherein the conical ratio is about 0.3.

10. The torch of claim 6, wherein the inner wall of the torch tube comprises a conical geometry having a conical ratio that is parallel the injector conical ratio.

11. The torch of claim 1, wherein the conical end comprises an axially straight portion, and wherein the cavity is defined in part by the axially straight portion.

12. The torch of claim 1, wherein a conical gap is defined by the annular channel between the conical end and the injector conical end, wherein the conical gap extends through at least a portion of the conical end such that the gas flow through the conical gap is parallel to at least the portion of the conical end, and wherein the conical gap is configured to axially accelerate the gas flow.

13. The torch of claim 12, wherein the conical gap is approximately 1 mm.

14. The torch of claim 1, wherein the support end of the torch tube upstream from the gas inlet is closed around the injector tube.

15. The torch of claim 1, wherein the torch is coupled to a mass spectrometer.

16. The torch of claim 1, wherein the torch is coupled to an optical emission spectrometer.

17. A method of using a torch for inductively coupled plasma, comprising:

positioning a conical end of a torch within a radio frequency (RF) load coil, wherein the torch comprises:
a torch tube having a support end and the conical end, wherein a portion of the conical end defines a cavity for confining the inductively coupled plasma;
an injector tube positioned within the torch tube, wherein the injector tube includes an injector inlet end for receiving a sample flow and an injector conical end; and
an annular channel defined between an outer wall of the injector tube and an inner wall of the torch tube, wherein the torch tube further comprises a gas inlet;
supplying a flow of gas to the gas inlet; and
operating the RF load coil to generate a plasma ball at the cavity.

18. The method of claim 17, wherein supplying the flow of gas to the gas inlet comprises directing the gas into the annular channel of the torch with an angular velocity.

19. The method of claim 17, wherein supplying the flow of gas to the gas inlet comprises flowing the gas in a spiral path within the annular channel.

20. The method of claim 17, wherein the plasma ball is generated at the cavity with a single gas flow, and wherein the single gas flow is the flow of gas.

21. The method of claim 17, further comprising delivering a sample to the plasma ball using the injector tube and analyzing the delivered sample using mass spectrometry.

22. The method of claim 17, further comprising delivering a sample to the plasma ball using the injector tube and analyzing the delivered sample using optical emission spectrometry.

* * * * *